US012329642B2

(12) United States Patent
Skaro et al.

(10) Patent No.: US 12,329,642 B2
(45) Date of Patent: Jun. 17, 2025

(54) TISSUE ANCHORS MINIMIZING MIGRATION AND MAXIMIZING ENGAGEMENT

(71) Applicant: Boston Scientific Scimed, Inc., Maple Grove, MN (US)

(72) Inventors: Jordan Skaro, San Jose, CA (US); Padraig J. Savage, Santa Rosa, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 219 days.

(21) Appl. No.: 17/478,005

(22) Filed: Sep. 17, 2021

(65) Prior Publication Data

US 2022/0096232 A1 Mar. 31, 2022

Related U.S. Application Data

(60) Provisional application No. 63/083,309, filed on Sep. 25, 2020.

(51) Int. Cl.
*A61B 17/84* (2006.01)
*A61B 17/86* (2006.01)
*A61F 2/24* (2006.01)

(52) U.S. Cl.
CPC .... *A61F 2/2445* (2013.01); *A61F 2220/0016* (2013.01)

(58) Field of Classification Search
CPC .. A61F 2/24; A61F 2/2445; A61F 2002/0817; A61F 2002/0888;
(Continued)

(56) References Cited

U.S. PATENT DOCUMENTS 5,782,865 A * 7/1998 Grotz ................. A61B 17/0642
606/328
5,976,139 A 11/1999 Bramlet
(Continued)

FOREIGN PATENT DOCUMENTS

| JP | 2002535068 A | 10/2002 |
|---|---|---|
| JP | 2008520270 A | 6/2008 |

(Continued)

OTHER PUBLICATIONS

International Search Report and Written Opinion dated Feb. 24, 2022 for International Application No. PCT/US2021/050827.

*Primary Examiner* — Seema Mathew
(74) *Attorney, Agent, or Firm* — Seager, Tufte & Wickhem, LLP

(57) ABSTRACT

A tissue anchor for securing an implantable device to tissue such as soft tissue. The anchor includes a tissue-engaging portion having a tissue-engaging configuration which enhances, improves, increases, etc., the engagement, grasp, purchase, etc. of the anchor with the body tissue in which the anchor is implanted. In some embodiments, the tissue-engaging portion cinches or pinches or compresses tissue between sections of the tissue-engaging portion to grab onto or otherwise engage tissue. In some embodiments, a section of the tissue-engaging portion expands or otherwise extends away from the other portions of the anchor to increase engagement of the anchor with the tissue. In some embodiments, a section of the tissue-engaging portion may flare outwardly to drive further into tissue in a direction transverse to other portions of the anchor.

20 Claims, 19 Drawing Sheets

(58) Field of Classification Search
CPC ............ A61F 2230/0091; A61F 2/2409; A61F 2220/0016; A61F 2/2448; A61F 2/2451; A61F 2/2454; A61F 2/246; A61F 2/2457; A61F 2/0811; A61F 2002/0858; A61B 17/0401; A61B 2017/0443; A61B 2017/0445; A61B 17/84; A61B 17/86; A61B 17/869; A61B 17/8615; A61B 17/8625

See application file for complete search history.

(56) References Cited

U.S. PATENT DOCUMENTS

| | | | | |
|---|---|---|---|---|
| 8,172,885 | B2* | 5/2012 | Songer | A61B 17/8047 606/289 |
| 9,622,862 | B2 | 4/2017 | Lashinski et al. | |
| 9,693,865 | B2* | 7/2017 | Gilmore | A61N 1/0573 |
| 9,788,948 | B2 | 10/2017 | Gilmore et al. | |
| 9,883,859 | B2* | 2/2018 | Conley | A61B 17/0485 |
| 10,058,319 | B2* | 8/2018 | Konrath | A61B 17/0485 |
| 10,470,756 | B2* | 11/2019 | Fallin | A61B 17/0401 |
| 10,548,585 | B2* | 2/2020 | Chan | A61B 17/0401 |
| 10,631,851 | B2* | 4/2020 | Balboa | A61B 17/0401 |
| 10,675,014 | B2* | 6/2020 | Chan | A61B 17/0401 |
| 11,116,556 | B2* | 9/2021 | Biedermann | A61B 17/866 |
| 11,298,163 | B2* | 4/2022 | Rezach | F16B 23/0069 |
| 12,208,006 | B2* | 1/2025 | Neumark | A61F 2/2445 |
| 2001/0000186 | A1 | 4/2001 | Bramlet et al. | |
| 2002/0055742 | A1 | 5/2002 | Lieberman | |
| 2002/0077631 | A1* | 6/2002 | Lubbers | A61B 17/0487 606/328 |
| 2003/0097132 | A1* | 5/2003 | Padget | A61B 17/8685 606/65 |
| 2006/0100622 | A1* | 5/2006 | Jackson | A61B 17/8625 606/301 |
| 2006/0106422 | A1 | 5/2006 | Del Rio et al. | |
| 2009/0292313 | A1 | 11/2009 | Anspach, III et al. | |
| 2010/0063542 | A1* | 3/2010 | van der Burg | A61B 17/0401 606/232 |
| 2012/0253355 | A1* | 10/2012 | Murray | B25B 15/005 606/104 |
| 2012/0265258 | A1 | 10/2012 | Garvey | |
| 2013/0041414 | A1* | 2/2013 | Epperly | A61B 17/7225 606/310 |
| 2013/0123857 | A1* | 5/2013 | Biedermann | A61B 17/84 606/303 |
| 2013/0238036 | A1* | 9/2013 | Sinha | A61B 17/88 606/317 |
| 2013/0338722 | A1* | 12/2013 | Yalizis | A61B 17/68 606/312 |
| 2014/0207196 | A1* | 7/2014 | Slagle | A61B 17/8625 606/305 |
| 2015/0223801 | A1* | 8/2015 | Ogdahl | A61F 2/0045 606/232 |
| 2017/0135816 | A1 | 5/2017 | Lashinski et al. | |
| 2020/0085478 | A1* | 3/2020 | McClintock | A61B 17/7059 |
| 2020/0100890 | A1* | 4/2020 | Hamilton | A61F 2/0811 |
| 2020/0138497 | A1* | 5/2020 | Morrison | A61B 17/869 |
| 2020/0155298 | A1 | 5/2020 | Krumme | |
| 2020/0298356 | A1* | 9/2020 | Witte | F16B 7/182 |
| 2020/0345496 | A1* | 11/2020 | Bishop | A61F 2/2457 |
| 2021/0068955 | A1 | 3/2021 | Bruner | |
| 2021/0161664 | A1 | 6/2021 | Krumpelmann et al. | |
| 2021/0290217 | A1* | 9/2021 | Biedermann | A61B 17/0485 |
| 2021/0307924 | A1* | 10/2021 | Glerum | A61B 17/8685 |
| 2022/0054122 | A1* | 2/2022 | Bowman | A61B 17/0401 |
| 2022/0265261 | A1* | 8/2022 | Hernandez | A61B 17/0401 |
| 2025/0032161 | A1* | 1/2025 | Mehl | A61B 17/1635 |

FOREIGN PATENT DOCUMENTS

| | | |
|---|---|---|
| JP | 2013-517830 A | 5/2013 |
| JP | 2014517739 A | 7/2014 |
| JP | 2020526316 A | 8/2020 |
| WO | 2011089601 A1 | 7/2011 |
| WO | 2021247960 A1 | 12/2012 |
| WO | 2019014155 A1 | 1/2019 |
| WO | 2020123719 A1 | 6/2020 |
| WO | 2021003505 A1 | 1/2021 |

* cited by examiner

TISSUE ANCHORS MINIMIZING MIGRATION AND MAXIMIZING ENGAGEMENT

PRIORITY

The present application is a non-provisional of, and claims the benefit of priority under 35 U.S.C. § 119 to, U.S. Provisional Application Ser. No. 63/083,309, filed Sep. 25, 2020, the disclosure of which is hereby incorporated herein by reference in its entirety for all purposes.

FIELD

The present disclosure relates generally to the field of implantable medical devices. More particularly, the present disclosure relates to the field of devices implantable into body tissue. In particular, the present disclosure relates to medical devices, systems, and methods for cardiac treatment, such as annuloplasty.

BACKGROUND

Mitral insufficiency (MI) (also referred to as mitral regurgitation or mitral incompetence) is a form of heart disease where the mitral annulus dilates excessively and the valve leaflets no longer effectively close, or coapt, during systolic contraction. Regurgitation of blood occurs during ventricular contraction and cardiac output may decrease as a result. Surgical and endoluminal annuloplasty techniques, including transcatheter repair, have been introduced that aim to restore a mitral valve to its native or an improved configuration, for example by implanting an annuloplasty ring or other implantable device around the valve annulus.

One difficulty encountered with implanting devices in the heart is anchoring and fixing an implant into soft material such as heart tissue for long periods without anchor migration or pullout.

Devices and systems and methods which may reinforce or strengthen the positioning or connection of an implantable device in an implant site, and/or reduce migration (shifting or loosening) of the implantable device with respect to the treatment site, and/or reduce potential tissue damage at the treatment site (such as when the implantable device is manipulated, such as cinched, to modify the valve annulus configuration, or later after the procedure has been completed) would be welcome.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a tissue anchor having a proximal end and a distal end, the distal end configured for insertion into body tissue, is disclosed, the tissue anchor comprising an anchor head at its proximal end, and an anchor shaft extending distally from the anchor head to the distal end of the anchor. The anchor shaft includes a tissue-engaging portion and a drive portion, the tissue-engaging portion being movable with respect to the drive portion to shift between an insertion configuration and a tissue-engaging configuration. The insertion configuration facilitates insertion of the anchor into tissue, and the tissue-engaging configuration enhances engagement of the anchor shaft with the tissue.

In some embodiments, the drive portion includes a lead screw configured to drive the anchor into tissue.

In some embodiments, the tissue-engaging portion includes an anchor section which compresses to pinch tissue therebetween when the tissue-engaging portion shifts from the insertion configuration to the tissue-engaging configuration. In some embodiments, the anchor section includes helical coils which move closer together as the tissue-engaging portion shifts from the insertion configuration to the tissue-engaging configuration to grasp tissue between the coils to enhance engagement of the anchor with the tissue.

In various embodiments, the tissue-engaging portion includes an anchor section which extends radially outwardly when the tissue-engaging portion shifts from the insertion configuration to the tissue-engaging configuration. In some embodiments, the anchor section buckles outwardly when the tissue-engaging portion shifts from the insertion configuration to the tissue-engaging configuration. In some embodiments, the anchor section flares radially outwardly when the tissue-engaging portion shifts from the insertion configuration to the tissue-engaging configuration. In some embodiments, the anchor section includes barbs which flare outwardly from a stored configuration when the tissue-engaging portion shifts from the insertion configuration to the tissue-engaging configuration. In some embodiments, the anchor section includes a helical coil with ends flaring outwardly when the tissue-engaging portion shifts from the insertion configuration to the tissue-engaging configuration.

In some embodiments, the drive portion is positioned within the tissue-engaging portion, and the tissue-engaging portion includes an outer anchor section movable with respect to the drive portion to shift between the insertion configuration and the tissue-engaging configuration.

In some embodiments, the tissue-engaging portion is positioned within the drive portion and includes an anchor section movable with respect to the drive portion from a stored position within the drive portion when the tissue-engaging portion is in the insertion configuration, and an extended position extending outwardly from the drive portion when the tissue-engaging portion is in the tissue-engaging configuration.

In various embodiments, a proximal end of the drive portion engages a proximal end of the tissue-engaging portion to inhibit relative rotational movement between the drive portion and the tissue-engaging portion when the tissue-engaging portion is in the insertion configuration, and the proximal end of the drive portion and the proximal end of the tissue-engaging portion are movable out of engagement to allow relative rotational movement between the drive portion and the tissue-engaging portion to shift the tissue-engaging portion into the tissue-engaging configuration. In some embodiments, relative rotational movement between the drive portion and the tissue-engaging portion allows axial movement of at least a portion of the tissue-engaging portion relative to the drive portion to allow the tissue-engaging portion to shift into the tissue-engaging configuration.

In accordance with various principles of the present disclosure, an implantable device is provided with a frame member, and at least one anchor coupled to the frame member and having a proximal end and a distal end, the distal end configured for insertion into body tissue. The anchor includes an anchor head at the proximal end of the anchor; an anchor shaft extending distally from the anchor head to the distal end of the anchor; and a tissue-engaging portion shiftable between an insertion configuration facilitating insertion of the anchor into tissue, and a tissue-engaging configuration enhancing engagement of the anchor within the tissue in which the anchor has been inserted.

In various embodiments, the anchor shaft includes the tissue-engaging portion and further includes a drive portion, the tissue-engaging portion being movable with respect to the drive portion to shift between the insertion configuration and the tissue-engaging configuration, the system further including an anchor cover configured to engage the anchor head to facilitate relative movement between the tissue-engaging portion and the drive portion. In some embodiments, the anchor cover is configured to hold the tissue-engaging portion axially with respect to the drive portion to allow the drive portion to be moved axially out of engagement with the tissue-engaging portion when the anchor is in the insertion configuration to allow the tissue-engaging portion to move with respect to the drive portion into the tissue-engaging configuration. In some embodiments, the anchor cover is configured to engage a proximal end of the tissue-engaging portion to inhibit rotation of the proximal end of the tissue-engaging portion relative to a proximal end of the drive portion, while relative rotation between the drive portion and the tissue-engaging portion allows axial movement of a distal end of the tissue-engaging portion to shift the tissue-engaging portion into the tissue-engaging configuration.

In accordance with various principles of the present disclosure, a method of implanting an implantable device in soft tissue includes advancing an anchor coupled to the implantable device into soft tissue; and, after the anchor has been inserted into the soft tissue, causing the anchor to shift from an insertion configuration to a tissue-engaging configuration in which the anchor has increased purchase on the tissue to enhance securement of the implantable device with respect to the tissue.

In various embodiments, the anchor includes a drive portion and a tissue-engaging portion, and the method further includes driving the drive portion into the tissue and causing the tissue-engaging portion to move with respect to the drive portion to increase engagement of the anchor with the tissue. In some embodiments, the method further includes rotating the drive portion to cause the tissue-engaging portion to move into the tissue-engaging configuration.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
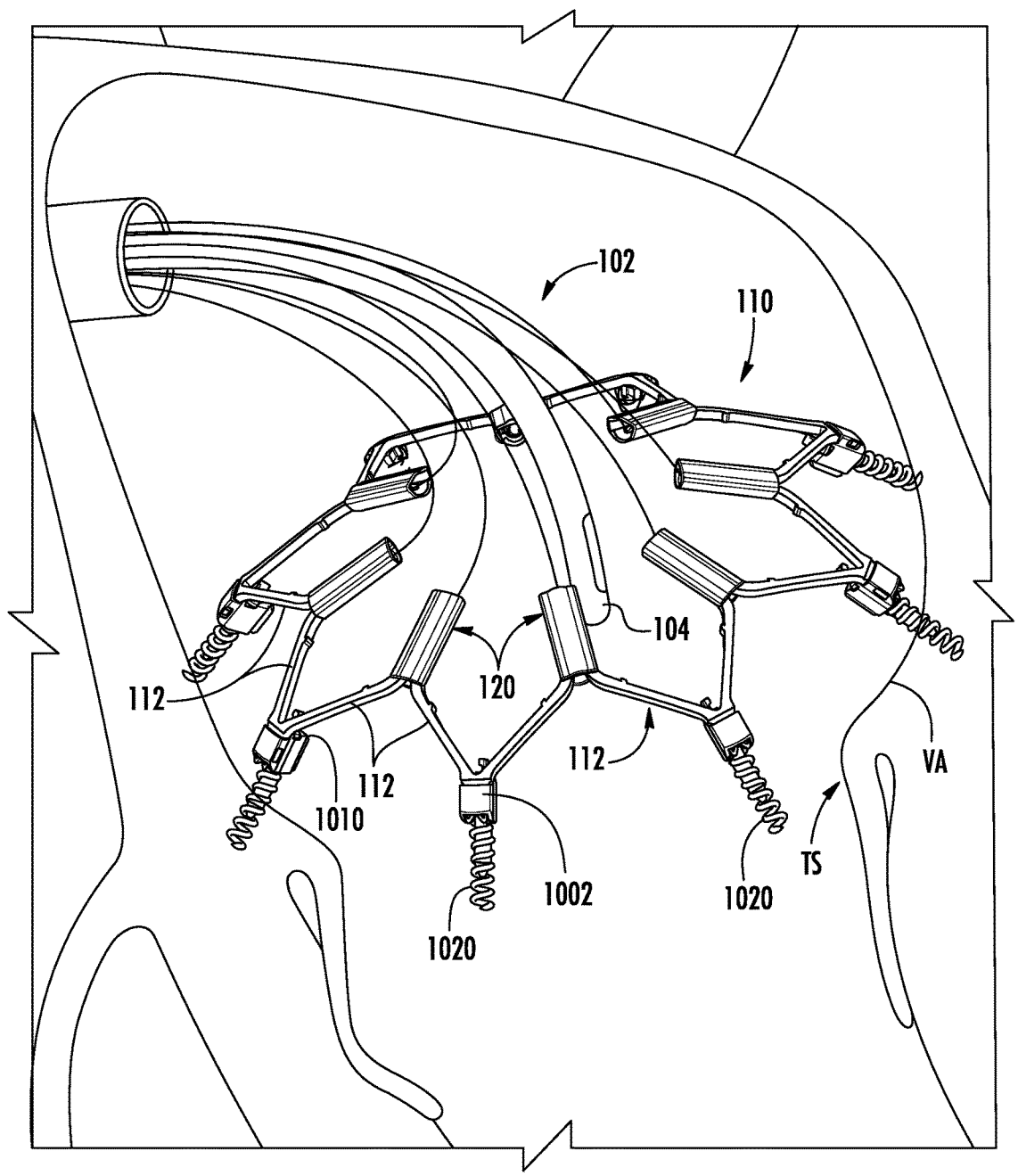
FIG. 1 is a schematic view of a human heart valve with an example of a heart valve implant device shown implanted in the valve annulus using anchors formed in accordance with various aspects of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, or a bore.

In accordance with principles of the present disclosure, an anchor is configured to improve engagement with tissue (e.g., soft tissue) for improved anchor retention and improved securement of an implantable device at a treatment site (e.g., tissue at a treatment site in or on a human body). In accordance with one aspect of the present disclosure, an anchor is configured to have at least one tissue-engaging portion which moves or shifts between an insertion configuration, facilitating insertion of the anchor into tissue, and a tissue-engaging configuration improving retention of the anchor in the tissue in which the anchor is implanted. In some embodiments, the anchor has an anchor head and an anchor shaft, and the tissue-engaging portion is a portion of the anchor shaft. In some embodiments, the anchor includes a drive portion coupled with the tissue-engaging portion and configured to drive the anchor into tissue. The drive portion may include a lead screw configured to be driven into and engaged with the tissue. In the insertion configuration, the tissue-engaging portion may be substantially compact, or otherwise positioned close to and/or aligned with the drive portion to facilitate insertion of the tissue-engaging portion with the drive portion into tissue. In some embodiments, the drive portion actuates the tissue-engaging portion to move between the insertion configuration and the tissue-engaging configuration. For instance, in some embodiments, relative movement between the tissue-engaging portion and the drive portion, such as relative rotational movement, allows or causes the tissue-engaging portion to move between the insertion configuration and the tissue-engaging configuration. In some embodiments, the tissue-engaging portion and the drive portion are selectively rotationally coupled together to rotate together, and selectively uncoupled to permit relative rotation therebetween.

An improved tissue anchor formed in accordance with various principles of the present disclosure includes a tissue-engaging portion having a tissue-engaging configuration which enhances, improves, increases, etc., the engagement, grasp, purchase, etc. of the anchor with the body tissue in which the anchor is implanted. In some embodiments, the tissue-engaging portion cinches or pinches or compresses tissue between sections of the tissue-engaging portion to grab onto or otherwise engage tissue. In some embodiments, a section of the tissue-engaging portion expands or otherwise extends away from the other portions of the anchor, such as to further embed into the tissue or to increase the footprint or surface area of the tissue-engaging portion with respect to the tissue, and/or to increase the hold in the tissue and to inhibit or prevent the anchor from backing out or otherwise and/or to minimize or eliminate tissue "walking". Alternatively or additionally, a section of the tissue-engaging portion may flare outwardly to drive further into tissue in a direction transverse to other portions of the anchor.

An improved anchor formed in accordance with one or more aspects or principles of the present disclosure may be provided on (e.g., coupled to or mounted on) an implantable device, and used to secure or anchor the implantable device in tissue at a treatment site. One or more anchors may be provided. An actuator or driver shaft or driver (such terms being used interchangeably herein without intent to limit) may engage the anchor to advance or drive the anchor into tissue, and, optionally, to retract the anchor if desired. In some embodiments, the anchor includes a latch or coupler configured to be engaged with the actuator or another latch provided on a delivery and/or deployment device provided and configured to deliver and/or deploy and/or adjust and/or otherwise maneuver or manipulate the implantable device.

In accordance with an aspect of the present disclosure, in an embodiment in which the tissue-engaging portion and the driver portion of the anchor are selectively rotationally coupled or uncoupled, the driver portion may be configured to cause the tissue-engaging portion to shift between the insertion configuration and the tissue-engaging configuration when in a rotationally coupled or uncoupled position with respect to the tissue-engaging portion. In some embodiments, the drive portion and the tissue-engaging portion rotate together to be driven into tissue. The drive portion and the tissue-engaging portion may then be disengaged or decoupled from each other, and the drive portion rotated with respect to the tissue-engaging portion to cause or allow the tissue-engaging portion to change in configuration from the insertion configuration to the tissue-engaging configuration. An actuator may be used to rotate the tissue-engaging portion and the drive portion together, as well as the drive portion individually (without also rotating the tissue-engaging portion). In some embodiments, the tissue-engaging portion and the drive portion are interengaged, coupled, interlocked, etc. (such terms being used interchangeably herein without intent to limit) to rotate together, and an anchor cover may be provided to disengage, uncouple, separate, etc. or otherwise allow separate actuation of the drive portion and the tissue-engaging portion, such as actuation of the drive portion separate from the tissue-engaging portion, to cause or allow the tissue-engaging portion to shift from an insertion configuration to a tissue-engaging configuration. An anchor cover may additionally, or alternatively, be used to maintain desired relative positions between the tissue-engaging portion and the drive portion.

In accordance with an aspect of the disclosure, an implantable device is provided with at least one improved anchor. The anchor may be considered to be a part of or independent of the implantable device. The implantable device has a body member or body or frame member or frame (such terms being used interchangeably herein without intent to limit) and one or more anchors are coupled to the implantable device, such as to the body or frame thereof, and are shaped and configured to affix or secure or anchor the implantable device with respect to tissue. One or more of the anchors is formed in accordance with various principles of the present disclosure to enhance, improve, increase, etc., the engagement, grasp, purchase, etc. of the anchor with the tissue in which the anchor is implanted, such as described above. The implantable device may be configured for custom reshaping of a heart valve, such as the mitral valve. In some embodiments, the frame is a generally tubular frame with a proximal end and a distal end, with at least one of the improved anchors extending distally from a distal end of the frame and advanceable into the heart tissue. In some embodiments, the frame is formed of a plurality of struts, adjacent struts forming a proximal apex at a proximal end of the frame and a distal apex at the distal end of the frame. Anchors formed in accordance with principles of the present disclosure may be provided on one or more distal apices to anchor the implantable device with respect to tissue. The improved configuration of the anchor may increase tissue engagement and/or anchor retention, and/or inhibit or prevent tissue "walking" and/or anchor backout, thereby increasing efficacy of the implantable device.

These and other beneficial aspects of an improved tissue anchor, and implantable device with improved anchors, and methods of use of an improved tissue anchor and deployment of an implant with one or more improved anchors are described in more detail below. Although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage, and other similar heart failure conditions. Moreover, the principles disclosed herein may be applied to other implantable devices beyond devices implanted in the heart.

Various embodiments of improved tissue anchors, and implantable devices with improved tissue anchors, and methods of using same, will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, it will be appreciated that in the following description, elements or components similar among the various illustrated embodiments of anchors are generally designated with the same reference numbers increased by 100 and redundant description is omitted. Common features are identified by common reference elements and, for the sake of brevity, the descriptions of the common features are generally not repeated. For purposes of clarity, not all components having the same reference number are numbered.

Figure 2:
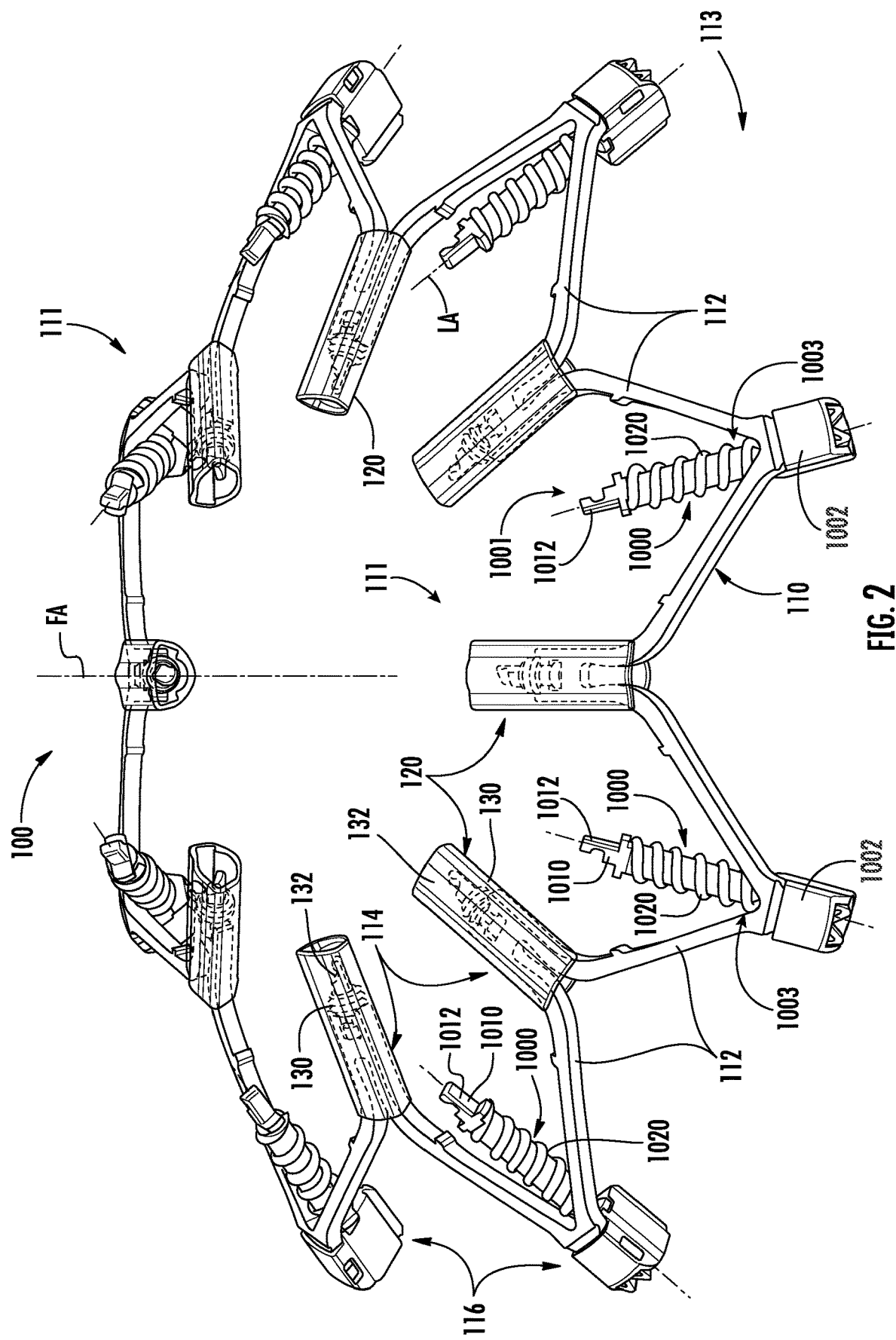
FIG. 2 is a perspective view of a heart valve implant device with an example of an anchor formed in accordance with various principles of the present disclosure.

An example of an implantable device 100 which may benefit from an anchor formed in accordance with one or more aspects of the present disclosure is illustrated in FIG. 1 being implanted in a heart valve annulus with the use of a deployment/delivery device or system 102, and in greater detail in FIG. 2. The implantable device 100 in this example is an implantable device for annuloplasty, such as for custom reshaping of a heart valve (e.g., the mitral valve, as illustrated, or the tricuspid valve), and is capable of moving between a collapsed configuration and an expanded configurations, and positions therebetween, to modify the shape of the valve annulus VA at which it is implanted/to which it is secured. An imaging catheter 104 may be used to locate the treatment site TS at which the implantable device 100 is to be delivered/deployed and implanted and/or to observe the configuration and/or position of the implantable device 100 during implantation and adjustment. An example of a steerable delivery device and system with various positioning and imaging capabilities is described in U.S. Pat. No. 10,335,275, titled Methods For Deployment Of Heart Valve Devices Using Intravascular Ultrasound Imaging, and issued on Jul. 2, 2019, which patent is incorporated herein by reference in its entirety for all purposes. Once at the treatment site TS, the implantable device 100, which may be held in a compressed or retracted or unexpanded (such terms being used interchangeably herein without intent to limit) configuration by a retention device or by the delivery device or otherwise, is allowed to expand for deployment and placement and implantation, as illustrated in FIG. 1. Expansion may occur naturally, for example if the frame is formed of a shape memory or super elastic material (e.g., Nitinol) that is biased towards an expanded state. In alternate embodiments, expansion may be mechanically controlled, for example through the use of a force applied within the frame using an expandable deployment device (e.g., an inflatable balloon or the like).

With reference to FIG. 2, the illustrated example of an implantable device 100 includes a frame member 110 that may be disposed about a heart valve or other cardiac feature. The frame member 110 may be generally symmetrical with respect to the central frame axis FA although it need not be symmetrical. The frame member 110 may form a generally tubular shape, the term "tubular" being understood herein to include circular as well as other rounded or otherwise closed shapes. The frame member 110 may be configured to change shape, size, dimension, and/or configuration. For example, the frame member 110 may assume various shapes, sizes, dimensions, configurations etc. during different phases of deployment such as during pre-delivery, delivery, tissue engagement, anchoring, adjustment (e.g., cinching), etc.

The frame member 110 may be formed from one or more struts 112 that may form all or part of the frame member 110. The struts 112 may include elongated structural members formed of a metal alloy, a shape memory material, such as an alloy of nickel titanium or other metals, metal alloys, plastics, polymers, composites, other suitable materials, or combinations thereof. In one embodiment, the struts 112 may be formed from the same, monolithic piece of material (e.g., tube stock). Thus, reference to struts 112 may refer to different portions of the same, coextensive component. Alternatively, reference to struts 112 may refer to components that are formed separately and attached together (optionally permanently, such as by welding or other methods). In some embodiments, the struts 112 may be separate components that are detachably coupled to form proximal apices 114 and distal apices 116. Alternatively, if formed from a monolithic piece of material, the material may be cut or otherwise formed to define proximal apices 114 and distal apices 116.

As shown in FIG. 2, in the illustrated example of an embodiment of an implantable device 100, a plurality of cinch collars 120 (alternately referenced as collars or sleeves or cinch sleeves or sliders or nuts, such terms being used interchangeably herein without intent to limit, reference being made generally to collars for the sake of convenience) are carried at the proximal end 111 of the frame member 110 on the proximal apices 114 of the frame member 110, and a plurality of tissue anchors 1000 are carried at a distal end 113 of the frame member 110, such as along the distal apices 116 of the frame member 110. In the illustrated embodiments, the proximal end 111 of the frame member 110 is directed proximally toward and engaged or carried by the delivery/deployment system 102, and the distal end 113 of the frame member 110 extends distally from the delivery/deployment system 102 and is the end engaged with the treatment site TS. It will be appreciated that alternate configurations of the frame member 110, such as depending on the manner and orientation in which the implantable device 100 is delivered, are within the scope and spirit of the present disclosure.

Advancement or withdrawal of the collar 120 with respect to the proximal apex 114 over which the collar 120 is positioned adjusts the relative positions of the struts 112 joined at such apex. Such adjustment results in adjustment of at least one of the size, shape, configuration, dimension, etc. of the frame member 110 (e.g., retraction/compression or expansion of the frame upon bringing adjacent struts 112 closer or further apart, respectively) to affect at least one of the size, shape, configuration, dimension, etc. of the treatment site TS (such as to restore or correct the shape of a valve annulus for proper functioning or competency thereof). The collars 120 may be adjusted in various manners, such as by engagement with a threaded collar actuator 130 engaging threads within the collars 120, rotation of the collar actuator 130 (held against axial movement) causing axial movement of the collars 120. A latch 132 may be provided on the collar actuator 130 for engagement by a latch of an actuator provided to actuate (e.g., move, advance, retract, etc.) the collar 120 as desired.

Generally, each anchor 1000 is associated with a different distal apex 116. In some embodiments the anchors 1000 translate through an anchor housing 1002 coupled to the frame member 110. The anchors 1000 are distally advanced with respect to the frame member 110 into the valve annulus VA to implant or to adjust the position of the frame member 110, and withdrawn to remove or to adjust the position of the frame member 110. The anchors 1000 may generally include an anchor head 1010 at the proximal end 1001 of the anchor 1000 and an anchor shaft 1020 extending distally from the anchor head 1010 towards the distal end 1003 of the anchor 1000. The anchor shaft 1020 may include a helical portion or section such that rotation of the anchors 1000 advances or retracts the anchors 1000 with respect to the frame member 110. The anchor shaft 1020 (such as in the form of a helical shaft) may be coupled to and extend through a portion of an associated distal apex 116 of the frame member 110, with or without an associated anchor housing 1002. A latch 1012 may be provided or formed on the anchor head 1010 and configured to be engaged by a corresponding latch of an actuator provided to actuate (e.g., move, advance, retract, etc.) the anchor 1000.

An anchor 1000 formed in accordance with various principles of the present disclosure has one more than one configuration, including an insertion configuration, such as a compact configuration facilitating insertion into tissue, and a tissue-engaging configuration in which the anchor 1000 is shaped to enhance engagement with tissue such as to enhance retention of an implantable device secured to the tissue via the anchor 1000. In some embodiments, an anchor 1000 having more than one configuration has an anchor shaft 1020 with at least two portions which are movable with respect to each other to shift the anchor shaft 1020 between the insertion configuration and the tissue-engaging configuration.

Figure 3:
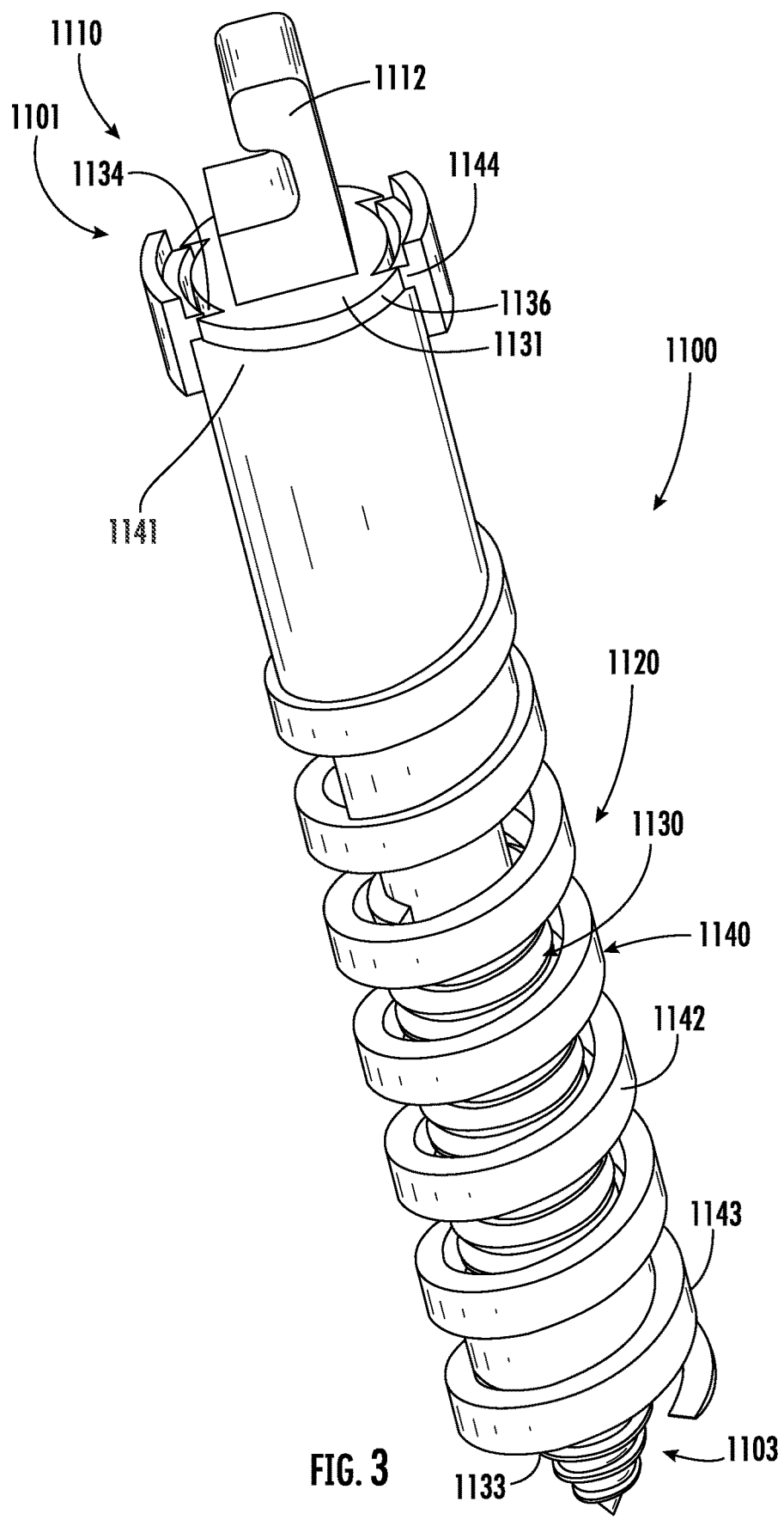
FIG. 3 is a perspective view of an embodiment of an anchor formed in accordance with various aspects of the present disclosure.
Figure 4:
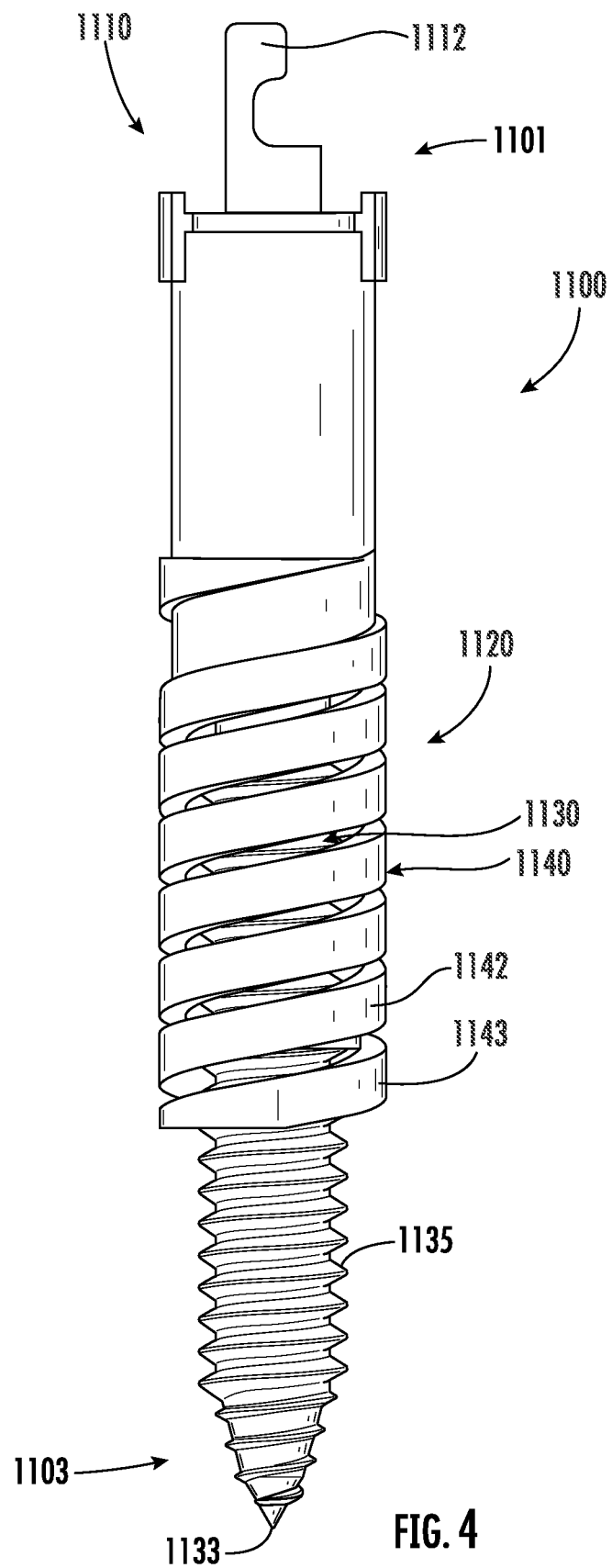
FIG. 4 is an elevational view of an anchor as in FIG. 3 in a tissue-engaging configuration in accordance with various aspects of the present disclosure.
Figure 5:
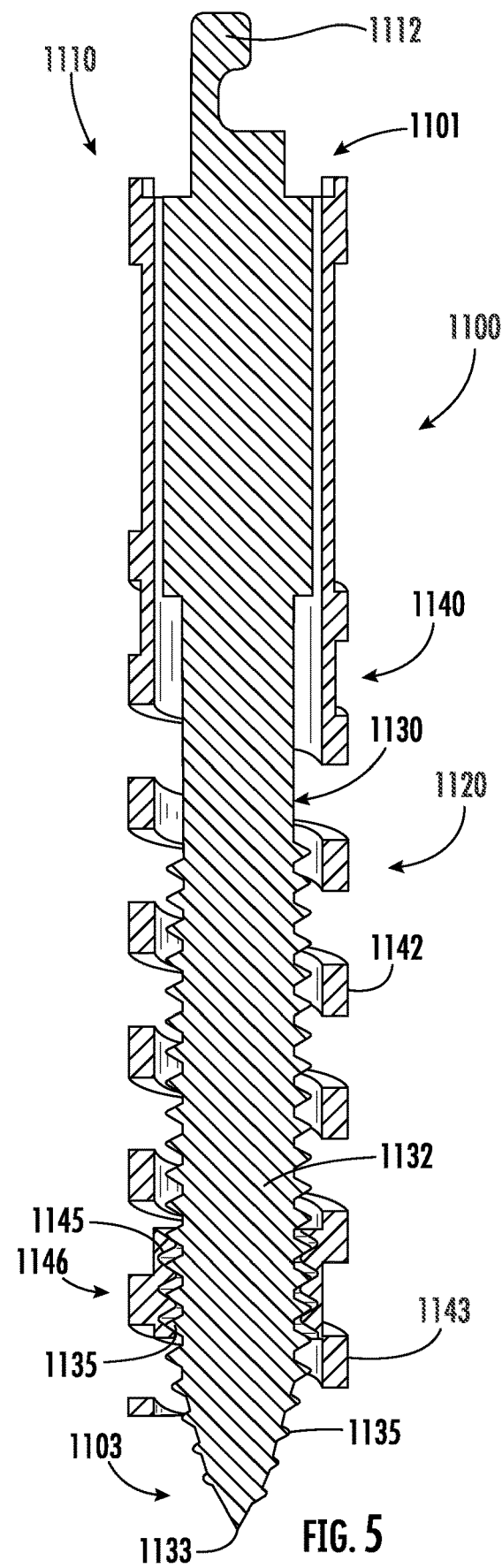
FIG. 5 is a cross-sectional view of an anchor as in FIG. 3.

In one embodiment formed in accordance with various principles of the present disclosure, as illustrated in FIG. 3-5, an anchor 1100 includes an anchor head 1110 at a proximal end 1101 of the anchor 1000, and an anchor shaft 1120 extending distally from the anchor head 1010 to the distal end 1103 of the anchor 1100. The illustrated anchor shaft 1120 includes a drive portion 1130 and a tissue-engaging portion 1140. Actuation of the anchor head 1110 (such as upon rotation of a latch 1112 extending proximally from the anchor head 1110) causes the drive portion 1130 to be driven into tissue (or retracted therefrom, when moved in the opposite direction). The drive portion 1130 and the tissue-engaging portion 1140 may be rotationally coupled to rotate together when the anchor 1100 is in an insertion configuration such as illustrated in FIG. 3. As may be appreciated, in the insertion configuration, the tissue-engaging portion 1140 extends substantially axially with respect to the longitudinal axis LA of the anchor 1100 and substantially aligned with at least the lead screw 1132 section of the drive portion 1130 of the anchor shaft 1120 such as to facilitate insertion into tissue.

Once the anchor shaft 1120 has been sufficiently advanced to secure the anchor 1100 to tissue, the anchor 1100 may be allowed to shift or transform into a tissue-engaging configuration, such as illustrated in FIG. 4. In a tissue-engaging configuration, the tissue-engaging portion 1140 is reconfigured, or shifted, or transformed, or otherwise (such terms being used interchangeably herein without intent to limit) into a configuration with an enhanced grasping or anchoring or tissue-engaging (such terms being used interchangeably herein with one another and other related terms, without intent to limit) shape or configuration. In the example illustrated in FIGS. 3 and 4, the tissue-engaging portion 1140 has an outer anchor section 1142 which changes or shifts in shape or configuration to increase its purchase on the tissue in which it has been inserted. In the embodiment of FIGS. 3-5, the outer anchor section 1142 is in the form a coiled outer anchor section which is compressed from an insertion configuration (such as illustrated in FIG. 3), in which there may be gaps between each turn of the coiled outer anchor section 1142 of the tissue-engaging portion 1140, to a tissue-engaging configuration (such as illustrated in FIG. 4), in which at least some of the turns of the coiled section have been moved closer together. The movement of the turns of the coiled outer anchor section 1142 of the tissue-engaging portion 1140 closer together may pinch or otherwise grasp the tissue in which the anchor 1100 has been inserted and extending between turns of the coiled outer anchor section 1142 when in an insertion configuration, thereby enhancing or increasing the purchase or grasping (such terms being used interchangeably herein without intent to limit) of the anchor 1100, via the tissue-engaging portion 1140, on the tissue.

As may be appreciated, in order for the anchor 1100 to shift between configurations in the embodiment of FIGS. 3-5, the drive portion 1130 and the tissue-engaging portion 1140, or at least sections thereof, move relative to each other. In the embodiment of FIGS. 3-5, the drive portion 1130 and the tissue-engaging portion 1140 selectively move axially (along the longitudinal axis LA of the anchor 1100) and rotationally together as well as with respect to each other. In particular, in the insertion configuration, the drive portion 1130 and the tissue-engaging portion 1140 are engaged or coupled together to rotate together during insertion of the anchor 1100 into tissue (such as facilitated by rotation of the latch 1112 on the anchor head 1110 to drive the anchor 1100 into the tissue), and generally do not move axially with respect to each other. To shift into a tissue-engaging configuration (such as illustrated in FIG. 4), the tissue-engaging portion 1140 is capable of moving relative to the drive portion 1130 to shift into a tissue-engaging configuration.

In the embodiment of FIGS. 3-5, the drive portion 1130 may be in the form of and/or include a lead screw 1132 configured to facilitate insertion of the anchor 1100 and/or penetration of tissue and/or driving of the anchor 1000 into the tissue. For example, the lead screw 1132 may include a sharpened distal end 1133 and outer threads 1135 facilitating penetration and/or advancement of the lead screw 1132 into tissue. Advancement of the lead screw 1132 advances the tissue-engaging portion 1140 of the anchor 1100 into the tissue, as well, generally when the drive portion 1130 and the tissue-engaging portion 1140 are rotationally coupled to rotate together. Such coupling may be achieved in a variety of manners within the scope of the present disclosure. For instance, in the embodiment of FIGS. 3-5, as may be most easily seen with reference to FIG. 3, the drive portion 1130 and the tissue-engaging portion 1140 are engaged at their respective proximal ends 1131, 1141 (which may be considered to form the anchor head 1110), such as with interlocking elements 1134, 1144 (e.g., a keyway or detent engaging a key or projection) to be rotationally locked against (e.g., restricted against) relative rotational movement. More particularly, in the illustrated embodiment, the proximal end 1131 of the drive portion 1130 includes a keyway or detent 1134 into which a key or projection 1144 on the proximal end 1141 of the tissue-engaging portion 1140 extends to inhibit or prevent rotational movement between the drive portion 1130 and the tissue-engaging portion 1140. It will be appreciated that a reverse arrangement (with a keyway or detent on the tissue-engaging portion 1140 and a key or projection in the drive portion 1130) are within the scope of the present disclosure. Optionally, a flange 1136 may be formed on the proximal end 1131 of the drive portion 1130 (with the keyway 1134 formed therein) to inhibit or prevent further distal movement of the drive portion 1130 with respect to the tissue-engaging portion 1140 and further proximal movement of the tissue-engaging portion 1140 with respect to the drive portion 1130.

Once the anchor 1100 is inserted sufficiently into tissue at the treatment site TS, the tissue-engaging portion 1140 may be actuated to shift into a tissue-engaging configuration. In the embodiment of FIGS. 3-5, the drive portion 1130 may actuate the tissue-engaging portion 1140 to shift into a tissue-engaging configuration. In particular, continued rotation of the drive portion 1130 may actuate the tissue-engaging portion 1140 to shift into a tissue-engaging configuration. Such actuation may be achieved by allowing a portion of the tissue-engaging portion 1140 to rotate with respect to the drive portion 1130 and allowing a distal portion of the tissue-engaging portion 1140 to move axially with respect to the drive portion 1130 while inhibiting the proximal portion of the tissue-engaging portion 1140 from moving axially with respect to a proximal portion the drive portion 1130. As may be appreciated with reference to FIG. 5, the tissue-engaging portion 1140 may include a drive section 1146 having inner threads 1145 engaging the outer threads 1135 on the lead screw 1132 section of the drive portion 1130. In some embodiments, the inner threads 1145 are formed on an interior surface of the drive section 1146 (such as on a cylindrical section having a greater axial extent along the longitudinal axis LA of the anchor 1100 than an individual turn of the coiled outer anchor section 1142). In other embodiments, a nut is formed in (e.g., machined as a part of) or separately formed and provided on the tissue-engaging portion 1140, the nut having inner threads 1145 for engaging the outer threads 1135 on the lead screw 1132. Generally, the drive section 1146 may be provided adjacent the distal end 1143 of the tissue-engaging portion 1140 to engage a distal end 1133 of the drive portion 1130. However, locations proximal to the illustrated location are within the scope of the present disclosure.

To actuate the tissue-engaging portion 1140, the drive portion 1130 and the tissue-engaging portion 1140 may be released from rotational engagement to be allowed to rotate relative to each other. In some embodiments, the drive portion 1130 may be moved axially relative to the tissue-engaging portion 1140 to move the interlocking elements 1134, 1144 out of engagement, such as by moving the drive portion 1130 axially with respect to the tissue-engaging portion 1140. If a flange 1136 is provided on the proximal end 1131 of the drive portion 1130, axial movement of the drive portion 1130 moves the flange 1136 proximally away from the projection 1144 on the proximal end 1141 of the tissue-engaging portion 1140 to allow rotation of the drive portion 1130 with respect to the tissue-engaging portion 1140 (e.g., by allowing the flange 1136 to rotate over the projection 1144). Continued rotation of the drive portion 1130 relative to the tissue-engaging portion 1140 while the drive section 1146 remains rotationally engaged with the lead screw 1132 causes the drive section 1146 to move axially proximally along the lead screw 1132 section of the drive portion 1130. As the drive section 1146 moves proximally, the coiled outer anchor section 1142 cinches or compresses the turns of the coil thereof, grasping or pinching tissue therebetween, thereby increasing grasp or purchase on the tissue in which the anchor 1100 has been inserted. Once the anchor 1100 is sufficiently secured, the drive portion 1130 and the tissue-engaging portion 1140 may be reengaged, such as to inhibit or prevent relative rotational movement therebetween, thereby holding the tissue-engaging portion 1140 in the tissue-engaging configuration illustrated in FIG. 5.

Figure 6:
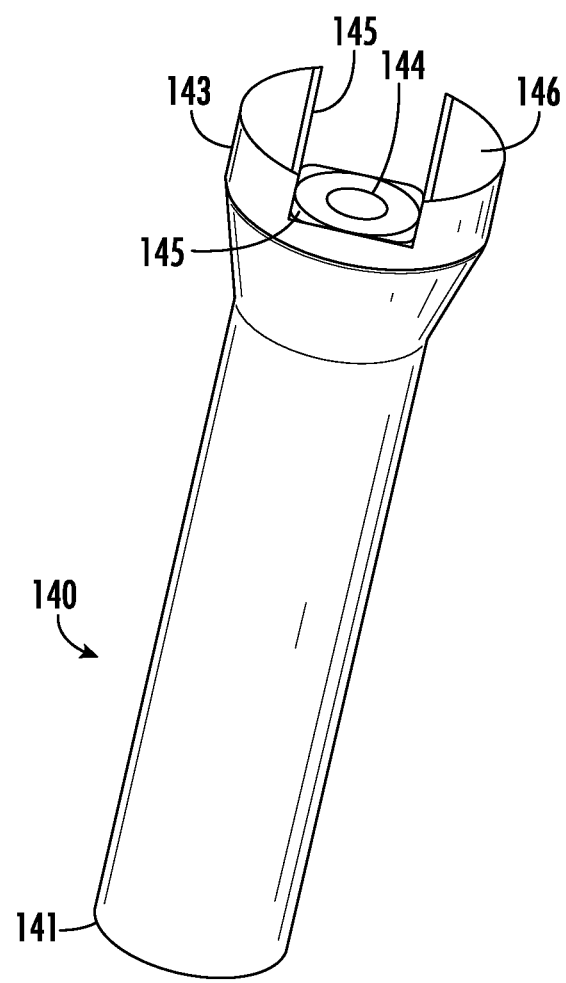
FIG. 6 is a perspective view of an example of anchor cover which may be used with an anchor formed in accordance with various principles of the present disclosure.
Figure 7:
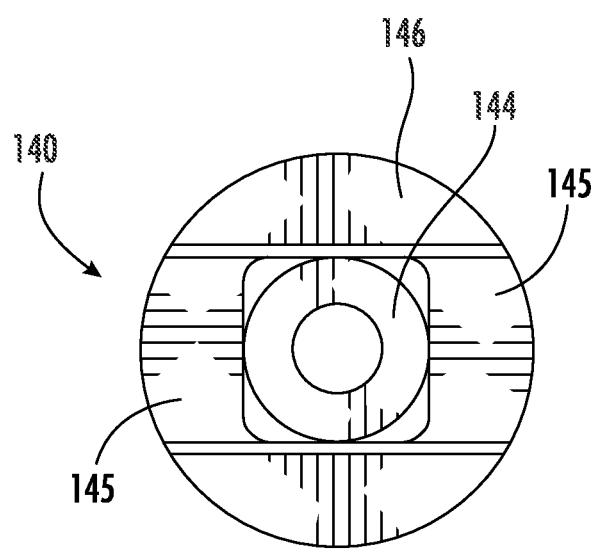
FIG. 7 is a top end view of an anchor cover as in FIG. 6.

As will be appreciated, the drive portion 1130 may be moved axially via engagement and axial movement of the latch 1112 on the proximal end 1131 of the drive portion 1130. To facilitate movement of the drive portion 1130 axially with respect to the tissue-engaging portion 1140, an anchor cover 140 such as illustrated in FIGS. 6 and 7 may be used. As may be appreciated with reference to FIG. 6, the anchor cover 140 includes an anchor-engaging distal end 143 configured to engage the proximal end 1101 of the anchor 1100. The anchor-engaging distal end 143 of the anchor cover 140 may include cutouts 145 in which the projections 1144 (which may be proximally-extending) on the proximal end 1141 of the tissue-engaging portion 1140 are received. The distally-extending anchor-engaging section 146 of the anchor cover 140 (which may be, for example, in the form of tabs) holds the proximal end 1141 of the tissue-engaging portion 1140 from moving proximally with the drive portion 1130 as the drive portion 1130 is axially moved proximally out of engagement with the tissue-engaging portion 1140. The anchor-engaging section 146 of the anchor cover 140 also laterally engages the projections 1144 on the tissue-engaging portion 1140 to inhibit rotation of the tissue-engaging portion 1140 relative to the drive portion 1130. The distal end 143 of the anchor cover 140 has a passageway 144, as may be see in FIG. 7, through which the proximal end 1131 of the drive portion 1130 may be proximally extended to facilitate disengagement from the tissue-engaging portion 1140 of the anchor shaft 1120 to allow relative rotation between the drive portion 1130 and the tissue-engaging portion 1140. To reengage the drive portion 1130 and the tissue-engaging portion 1140, tension on the latch 1212 on the proximal end 1131 of the drive portion 1130 may be released.

Figure 8:
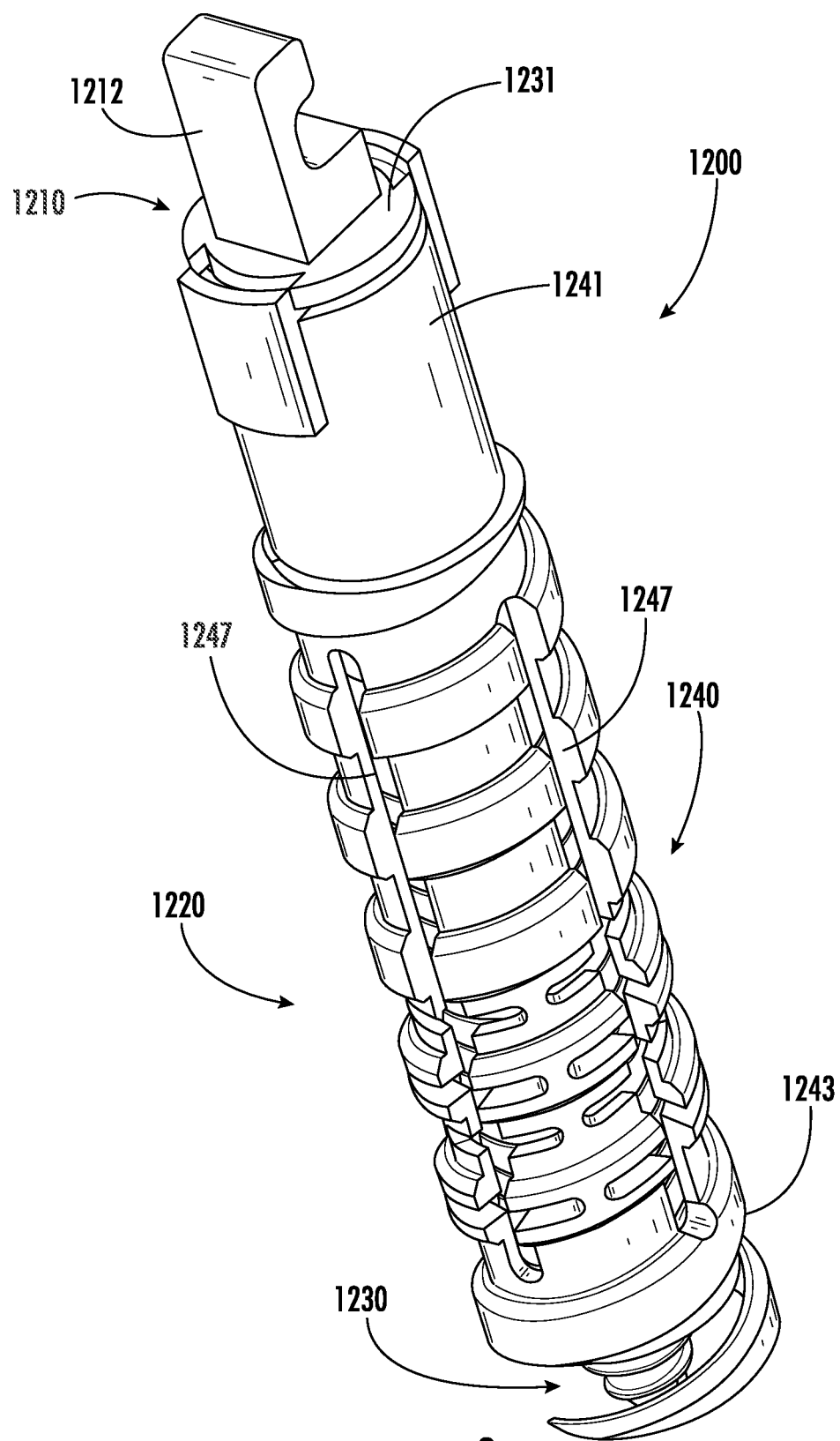
FIG. 8 is a perspective view of another embodiment of an anchor formed in accordance with various aspects of the present disclosure.
Figure 9:
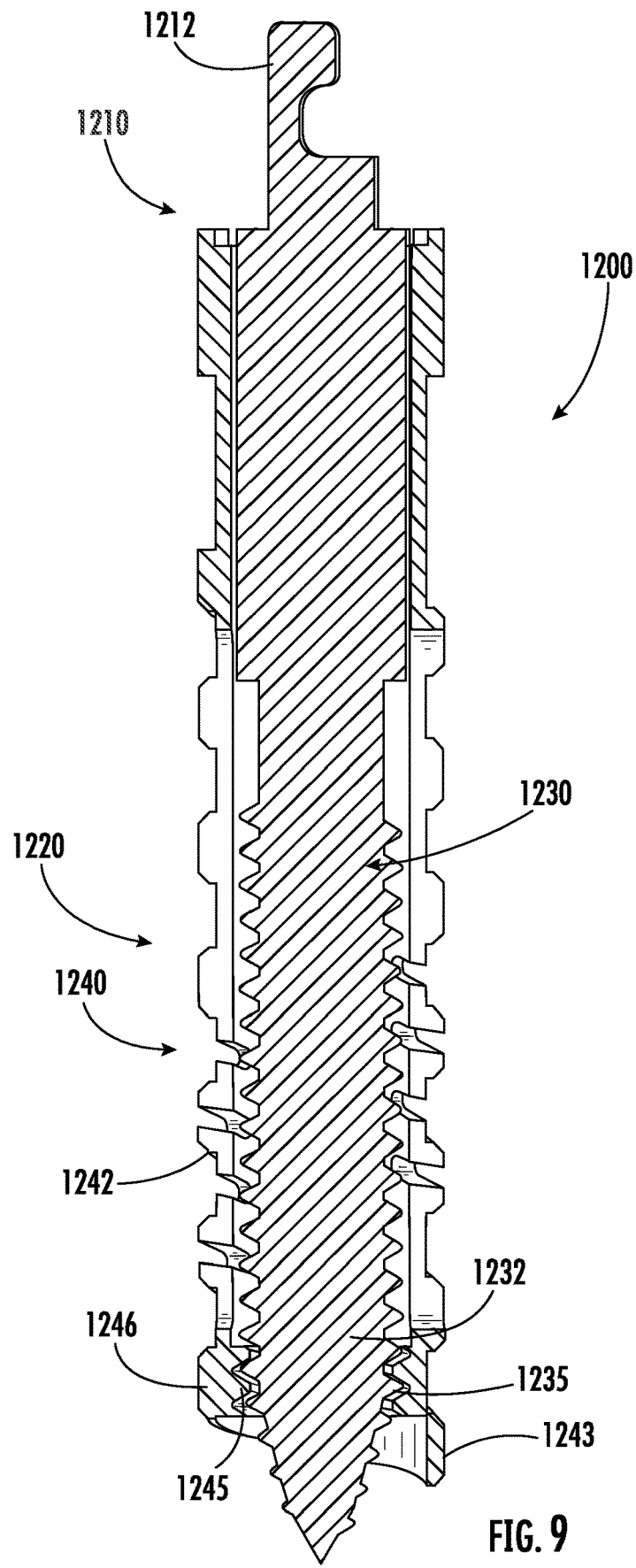
FIG. 9 is a cross-sectional view of an anchor as in FIG. 8.
Figure 10:
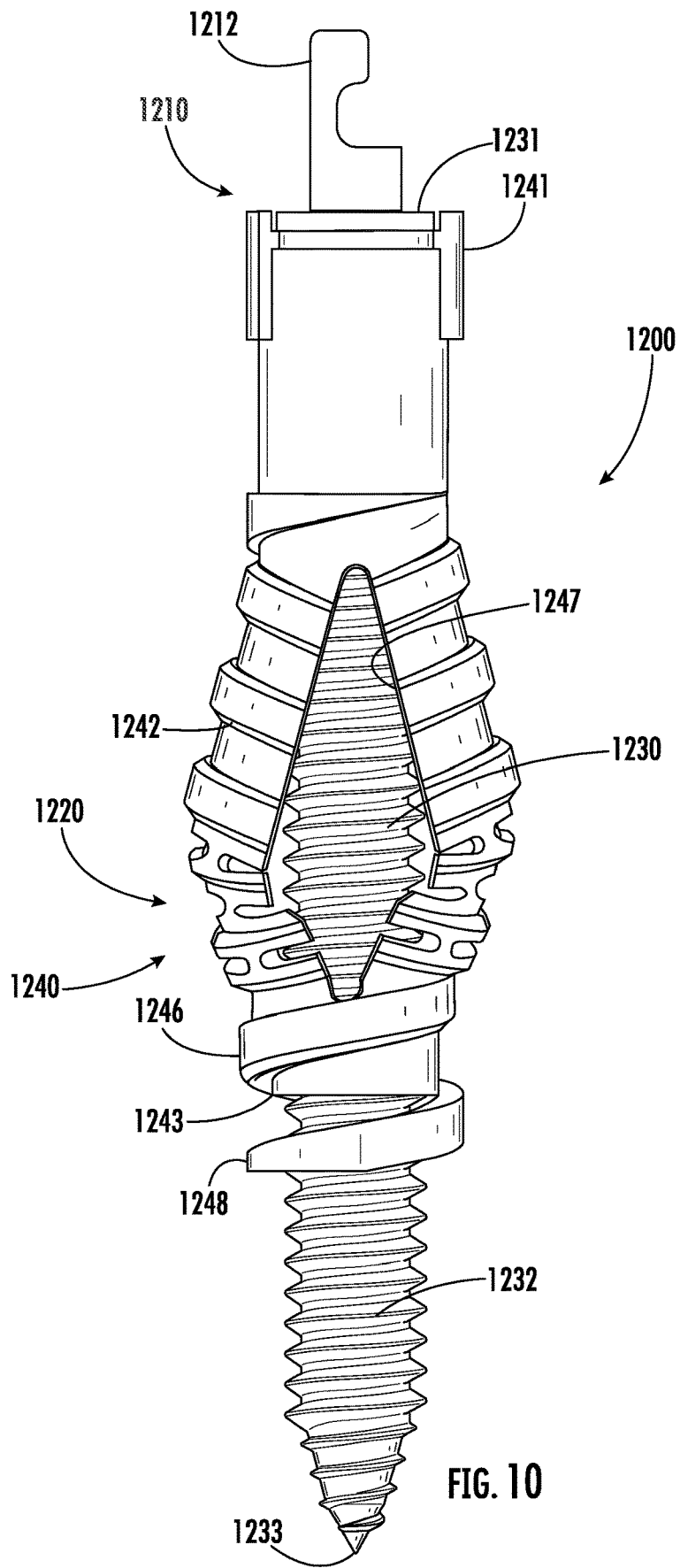
FIG. 10 is an elevational view of an anchor as in FIG. 8 in a tissue-engaging configuration in accordance with various aspects of the present disclosure.

It will be appreciated that various other configurations of anchors having a shaft with portions shifting between more than one configuration are within the scope of the present disclosure. Another embodiment of an anchor 1200 formed in accordance with principles of the present disclosure with an anchor shaft 1220 (extending distally from the anchor head 1210) which shifts between more than one configuration is illustrated in FIGS. 8-10. The anchor 1200 of FIGS. 8-10 has a tissue-engaging portion 1240 which moves between an insertion configuration (as illustrated in FIG. 8 and FIG. 9), in which the tissue-engaging portion 1240 extends substantially axially with respect to the longitudinal axis LA of the anchor 1200 and substantially aligned with at least the lead screw 1232 section of the drive portion 1230 of the anchor shaft 1220 (such as to facilitate insertion into tissue), and a tissue-engaging configuration, in which the tissue-engaging portion 1240 has an outer anchor section 1242 which changes or shifts in shape or configuration, such as by expanding or extending outwardly, to enhance engagement of the anchor 1200 with the tissue in which it is implanted. More particularly, as may be appreciated with reference to FIG. 10, the outer anchor section 1242 buckles or bows outwardly in the tissue-engaging configuration when the distal end 1243 of the tissue-engaging portion 1240 moves proximally.

Similar to the anchor 1100 illustrated in FIGS. 3-5, the tissue-engaging portion 1240 of the anchor 1200 of FIGS. 8-10 may include a drive section 1246 having inner threads 1245 engaging outer threads 1235 on the lead screw 1232 section of the drive portion 1230, as illustrated, for example, in FIG. 9. The proximal ends 1231, 1241 of the drive portion 1230 and the tissue-engaging portion 1240, respectively, may be moved into and out of engagement to rotate together (and may be considered together to form the anchor head 1210 of the anchor 1200) or not, such as described above with respect to the embodiment of FIGS. 3-5. Accordingly, for the sake of brevity, reference is made to the description of the engagement and movements of the drive portion 1130 and the tissue-engaging portion 1140 of the anchor 1100 of FIGS. 3-5, the general principles of which may be applied to the drive portion 1230 and the tissue-engaging portion 1240 of the anchor 1200 of FIGS. 8-10. Once the drive portion 1230 has been disengaged from the tissue-engaging portion 1240 (such as by being moved proximally to move the proximal ends 1231, 1241 of the drive portion 1230 and the tissue-engaging portion 1240 out of rotationally locked engagement), and is continued to be rotated (such as upon engagement and rotation of the latch 1212 by a drive actuator), the inner threads 1245 of the drive section 1246 ride proximally along the outer threads 1235 on the lead screw 1232 section of the drive portion 1230. Because the proximal end 1241 of the tissue-engaging portion 1240 is held against axial movement (such as by an anchor cover 140, as illustrated in FIGS. 7 and 8, and as described with reference to the embodiment of FIGS. 3-5), the drive section 1246 (and the distal end 1243 of the tissue-engaging portion 1240) moves proximally, causing the outer anchor section 1242 to buckle outwardly. In some embodiments, the outer anchor section 1242 of the tissue-engaging portion 1240 is defined by longitudinally extending slits 1247 in the tissue-engaging portion 1240 between the proximal end 1241 and the distal end 1243 of the tissue-engaging portion 1240, allowing buckling or expansion or outward extension (such terms being used interchangeably herein without intent to limit) of the outer anchor section 1242. Laser cuts may bias the walls of the outer anchor section 1242 to buckle distally/outwardly in the desired configuration.

Similar to the embodiment of FIGS. 3-5, the inner threads 1245 of the drive section 1246 of the anchor 1200 of FIGS. 8-10 may be formed directly on an interior surface of the drive section 1246 or a nut is formed in (e.g., machined as a part of) or separately formed and provided on the tissue-engaging portion 1240. Generally, the drive section 1246 may be provided adjacent the distal end 1243 of the tissue-engaging portion 1240 to engage a distal end 1233 of the drive portion 1230. However, locations proximal to the illustrated location are within the scope of the present disclosure. For instance, the distal end 1243 of the tissue-engaging portion 1240 may include a leading distal tip 1248 to assist the optionally sharpened distal 1233 of the lead screw 1232 in penetrating tissue.

Figure 11:
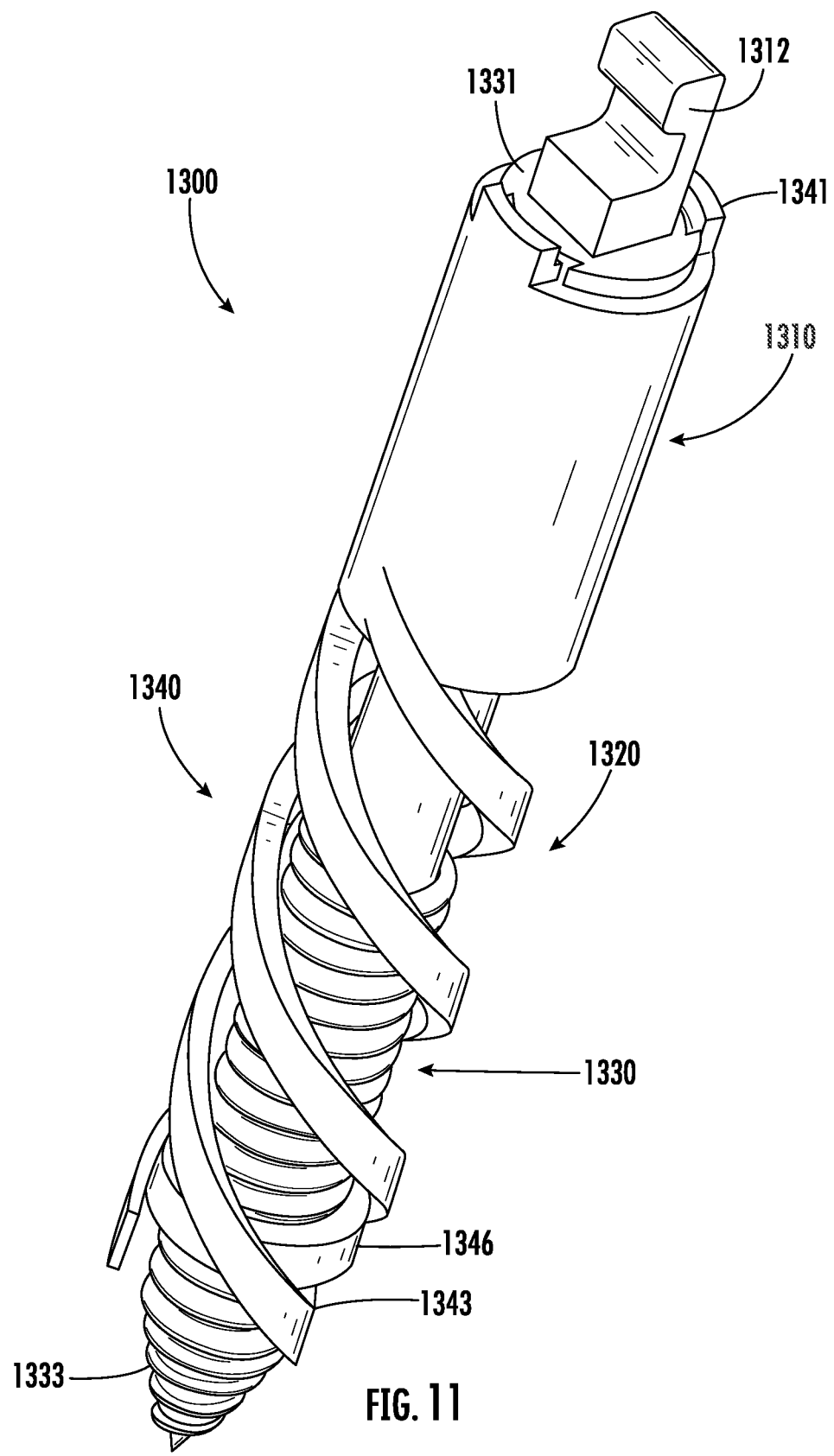
FIG. 11 is a perspective view of another embodiment of an anchor formed in accordance with various aspects of the present disclosure.
Figure 12:
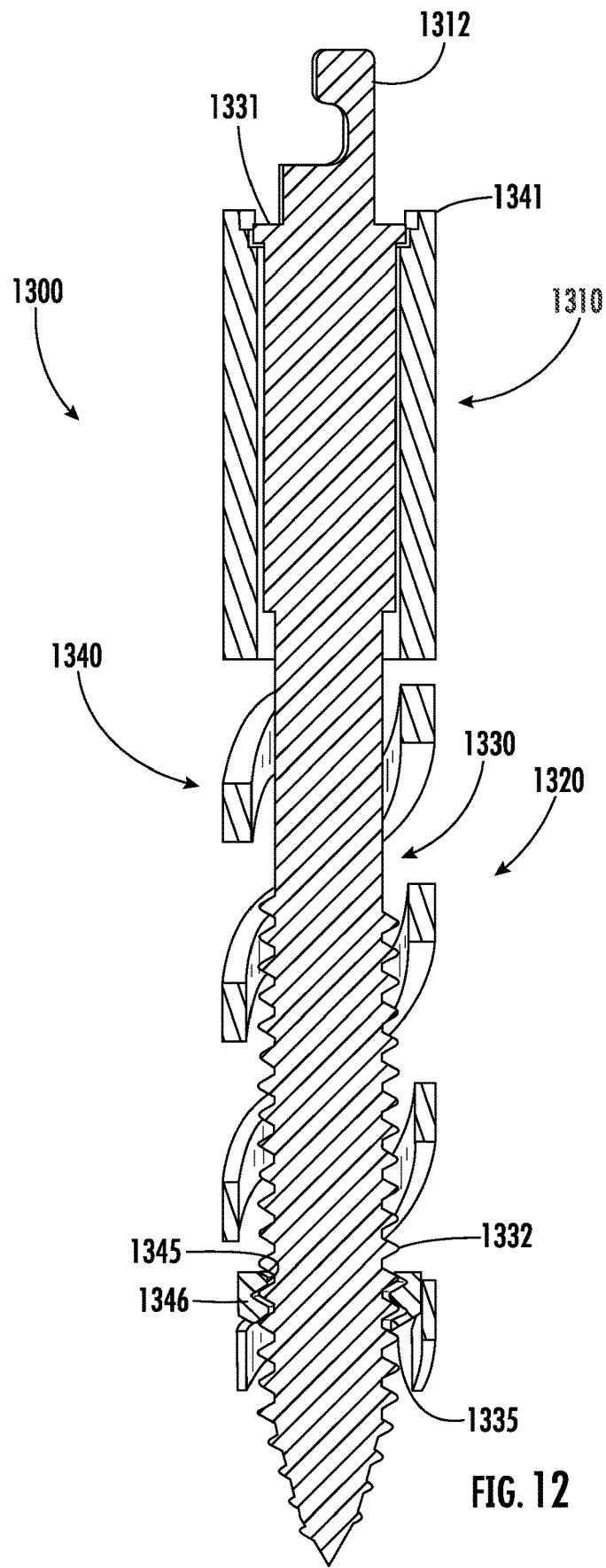
FIG. 12 is a cross-sectional view of an anchor as in FIG. 11.
Figure 13:
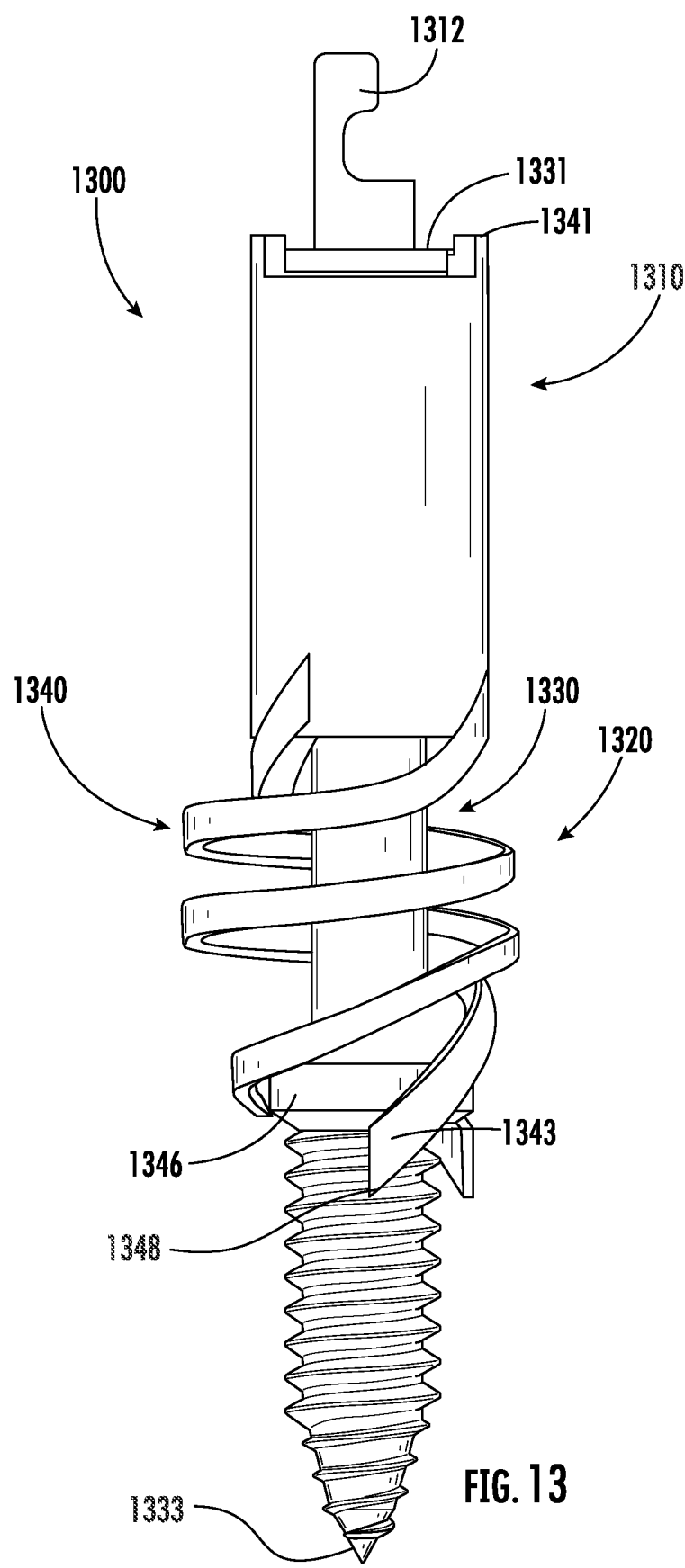
FIG. 13 is an elevational view of an anchor as in FIG. 11 in a tissue-engaging configuration in accordance with various aspects of the present disclosure.

Another embodiment of an anchor 1300 having an anchor shaft 1320 shiftable or movable between an insertion configuration, in which the anchor shaft 1320 (extending distally from the anchor head 1310) is shaped and configured to facilitate insertion into tissue, and a tissue-engaging configuration, in which a tissue-engaging portion 1340 expands or extends outwardly to enhance or increase the engagement of the anchor shaft 1320 with the tissue in which it is inserted, is illustrated in FIGS. 11-13. Instead of longitudinal slits facilitating expansion of the tissue-engaging portion 1340 of the anchor 1300, the outer anchor section 1342 of the tissue-engaging portion 1340 of the anchor 1300 illustrated in FIGS. 11-13 is formed of a plurality (e.g., three) helical coils. A drive section 1346 of the tissue-engaging portion 1340 of the anchor shaft 1320 includes inner threads 1345 engaging outer threads 1335 on the lead screw 1332 section of the drive portion 1330 of the anchor 1300. As the drive section 1346 moves proximally (such as by rotation of the drive portion 1330 relative to the tissue-engaging portion 1340 with the proximal ends 1331, 1341, along the anchor head 1310, substantially restrained against relative axial movement, such as by engagement thereof with an anchor cover 140 as described above), the helical coils of the outer anchor section 1342 expand outwardly and also may contract or compress axially, thereby further engaging the anchor 1300 into the tissue as well as pinching or holding tissue between coils of the tissue-engaging portion 1340. If desired, the distal ends of one or more of the helical coils of the outer anchor section 1342 may include sharp ends or hooks 1348 to facilitate driving of the tissue-engaging portion 1340 of the anchor shaft 1320 into tissue. The distal end 1333 of the lead screw 1332 may have a sharpened end as well. In some embodiments, the helical coils may be configured to flare or splay outwardly, as the tissue-engaging portion 1340 moves into the tissue-engaging configuration, to further increase the footprint of the tissue-engaging portion 1340 within the tissue.

It will be appreciated that although the drive section 1346 of the tissue-engaging portion 1340 is shown adjacent the distal end 1343 of the tissue-engaging portion 1340, the drive section 1346 may be positioned further proximally if further independent movement of the distal ends of the helical coils of the outer anchor section 1342 is desired.

Moreover, it will be appreciated that the drive section 1346 may be formed as a separate piece (e.g., a nut) welded or machined on the tissue-engaging portion 1340, or formed (e.g., laser cut) from a solid piece or section of the tissue-engaging portion 1340. Other features and components and sections of the anchor 1300 of FIGS. 11-13 can be arranged and operate in substantially the same or similar manners as corresponding features and components and sections of the anchor 1100 of FIGS. 3-5 and/or the anchor 1200 of FIGS. 8-10. Accordingly, for the sake of brevity and convenience, and without intent to limit, common elements with common functions are indicated with the same reference characters differing in value by 100, reference being made to the above descriptions of similar elements and operations.

Figure 14:
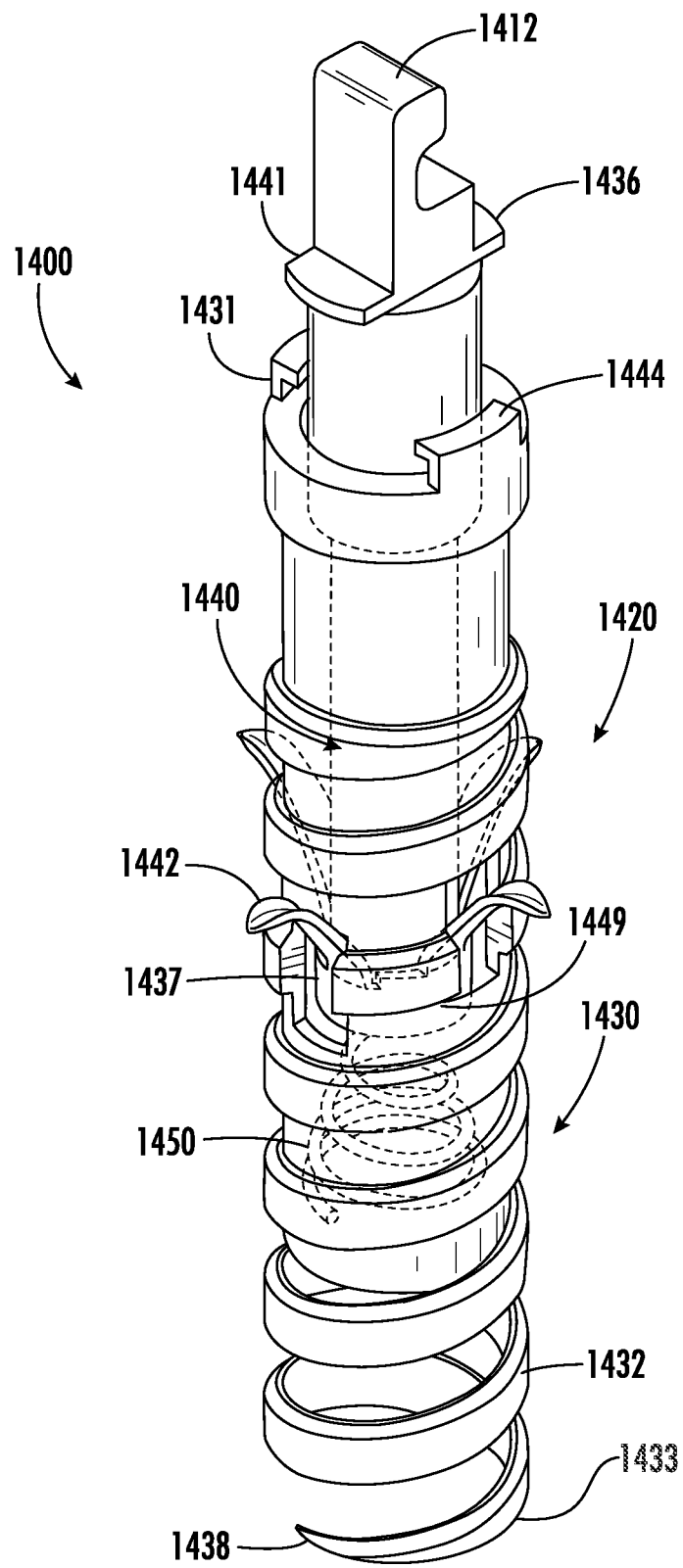
FIG. 14 is a perspective view of another embodiment of an anchor formed in accordance with various aspects of the present disclosure, and shown in a tissue-engaging configuration in accordance with various aspects of the present disclosure.
Figure 15:
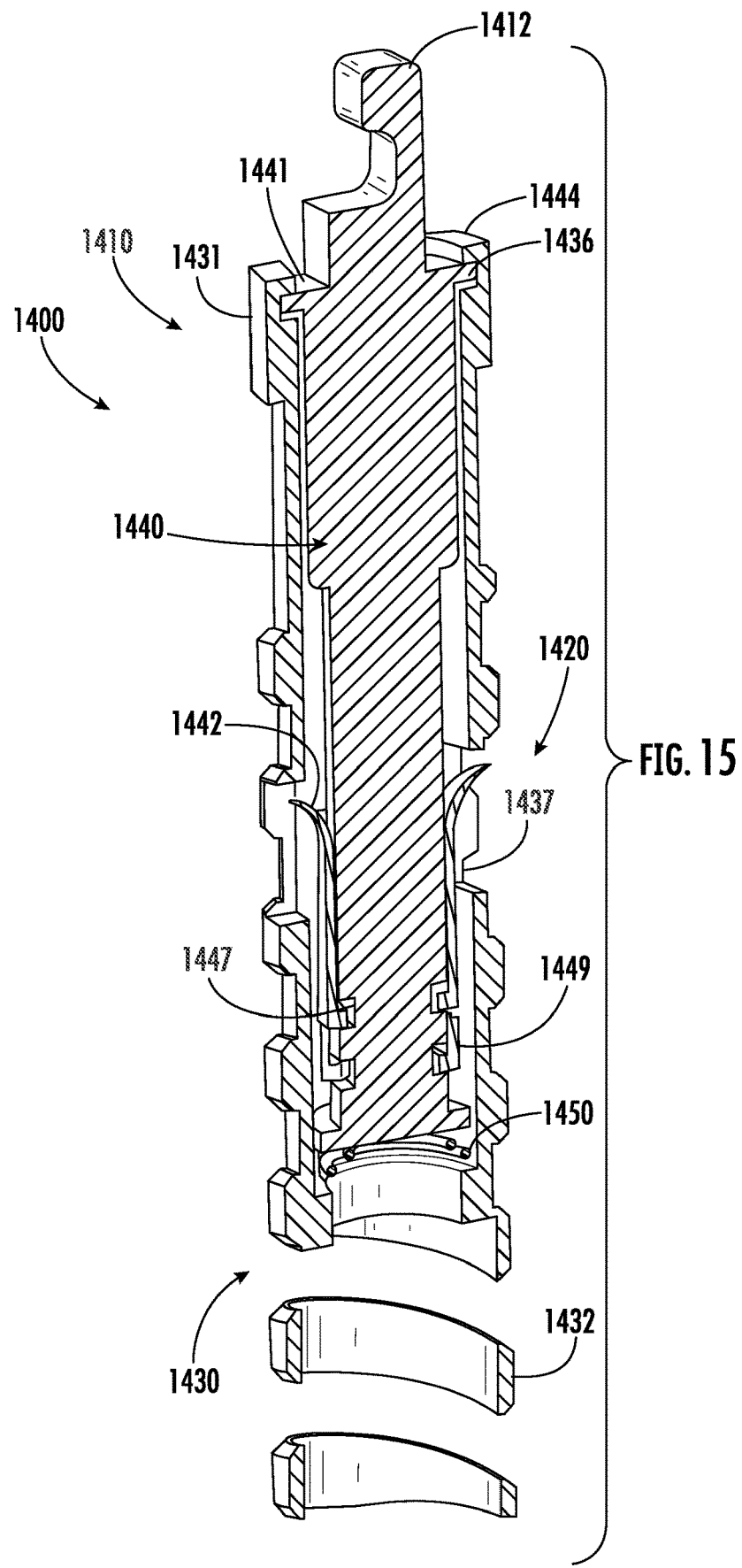
FIG. 15 is a perspective cross-sectional view of an anchor as in FIG. 15 in an insertion configuration in accordance with various aspects of the present disclosure.
Figure 16:
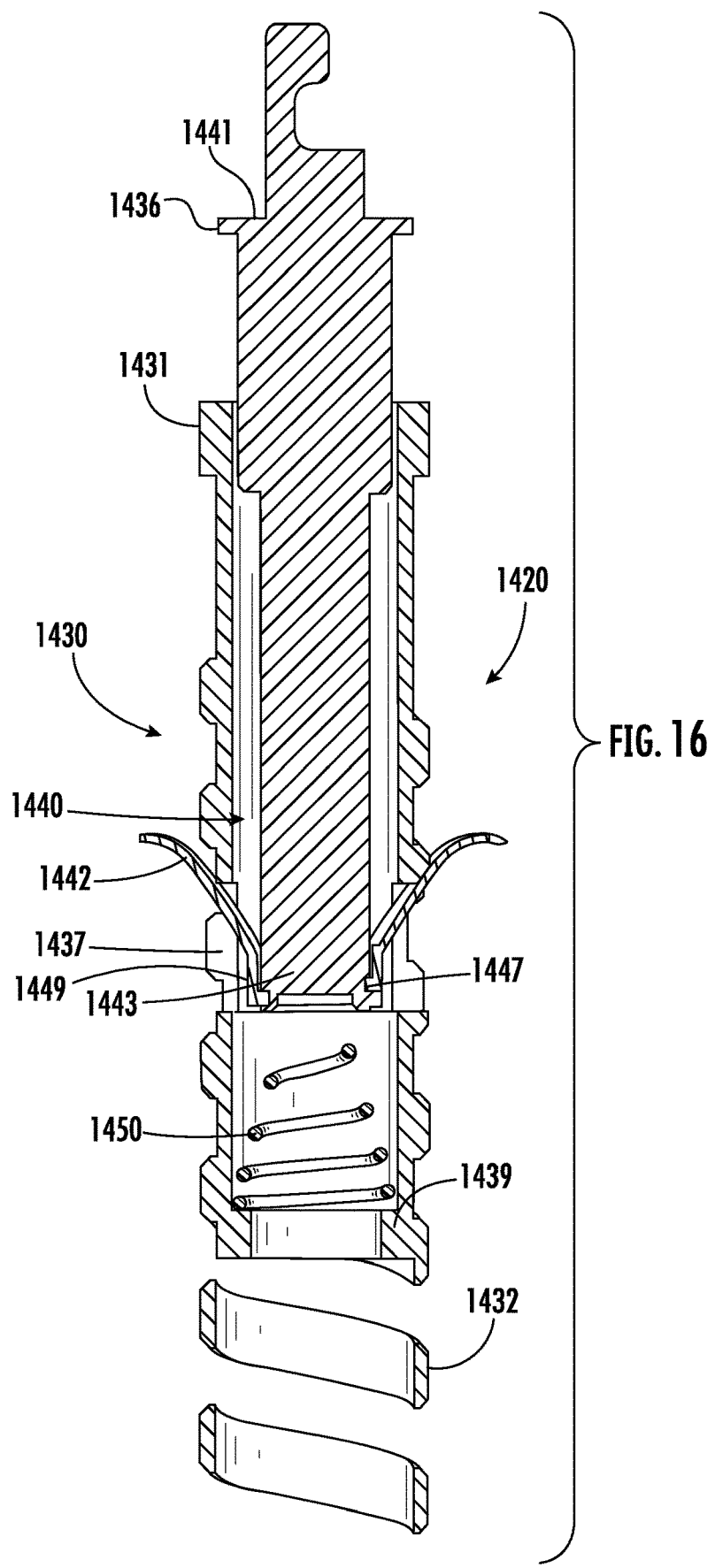
FIG. 16 is cross-sectional view of an anchor as in FIG. 14 in a tissue-engaging configuration in accordance with various aspects of the present disclosure.

Another embodiment of an anchor 1400 having an anchor shaft 1420 shiftable or movable between an insertion configuration, in which the anchor shaft 1420 is shaped and configured to facilitate insertion into tissue, and a tissue-engaging configuration, in which a tissue-engaging portion 1440 expands or extends outwardly to enhance or increase the engagement of the anchor shaft 1420 with the tissue in which it is inserted, is illustrated in FIGS. 14-18. In contrast with the above-described embodiments of anchors 1200, 1300, with a tissue-engaging portion 1240, 1340 with an outer anchor section 1242, 1342 positioned outside or around an inner drive portion 1230, 1330 of the anchor 1200, 1300, the tissue-engaging portion 1440 of the anchor 1400 of FIGS. 14-18 is positioned within an outer drive portion 1430 of the anchor shaft 1420. The outer drive portion 1430 of the embodiments of FIGS. 14-18 is in the form of a helical lead screw 1432 which may be driven into tissue such as by engaging a leading (optionally sharpened) distal tip 1438 at the distal end 1433 of the lead screw 1432 thereof with tissue to penetrate the tissue, and then rotating the drive portion 1430 (such as by rotating the proximal end 1431 thereof, along the anchor head 1410, with an anchor cover 140) to advance the anchor shaft 1420 into the tissue. The tissue-engaging portion 1440 has one or more resiliently biased tissue-engaging barbs 1442 which may extend through openings or windows 1437 in the drive portion 1430 of the anchor shaft 1420, as shown in FIG. 14 and FIG. 16, to extend into the tissue in which the anchor shaft 1420 has been inserted to increase the footprint of the anchor shaft 1420 and/or to improve engagement of the anchor shaft 1420 with the tissue.

To shift the tissue-engaging portion 1440 of the anchor 1400 of FIGS. 14-16 from an insertion configuration to a tissue-engaging configuration, the tissue-engaging portion 1440 is allowed to move relative to the drive portion 1430. In the insertion configuration, one or more outwardly-extending flanges 1436 on a proximal end 1441 of the tissue-engaging portion 1440 are held by shoulders or flanges 1444 on a proximal end 1431 of the drive portion 1430, as illustrated in FIG. 15, inhibiting relative axial movement between the tissue-engaging portion 1440 and the drive portion 1430. Rotation of the tissue-engaging portion 1440 relative to the drive portion 1430 releases the flanges 1436, and a biasing element 1450 (e.g., a spring) biases the tissue-engaging portion 1440 proximally with respect to the drive portion 1430, as illustrated in FIGS. 14 and 16. As may be appreciated with reference to FIG. 16, the biasing element 1450 may be positioned between a distal end 1443 of the tissue-engaging portion 1440 and a ledge 1439 within the drive portion 1430, though other arrangements are within the scope of the present disclosure. The tissue-engaging barbs 1442 may thus move from a position in which they are restrained or confined within the drive portion 1430 (such as illustrated in FIG. 15) to a position in which the tissue-engaging barbs 1442 may extend outwardly from the anchor shaft 1420, such as illustrated in FIGS. 14 and 16. The tissue-engaging barbs 1442 may be resiliently biased to extend outwardly once positioned next to the windows 1437 in the drive portion 1430, such as upon axial proximal movement of the tissue-engaging portion 1440 relative to the drive portion 1430. In some embodiments, the tissue-engaging barbs 1442 can be shape set to prevent misalignment with the windows 1437 while unlocking the respective proximal ends 1431, 1441 of the drive portion 1430 and the tissue-engaging portion 1440 of the anchor shaft 1420.

The tissue-engaging barbs 1442 may be formed separately from other sections of the tissue-engaging portion 1440 and engaged therewith. For instance, the tissue-engaging barbs 1442 may extend from a ring or collar or base 1449 (such terms being used interchangeably herein without intent to limit) having a section engaging within one or more grooves 1447 in the exterior of the tissue-engaging portion 1440. The tissue-engaging barbs 1442 extend through the windows 1437 in the drive portion 1430, and may thereby be restrained against rotational movement with respect to the tissue-engaging portion 1440 once extended therethrough. As such, the tissue-engaging barbs 1442 need not be restrained against rotational movement with respect to the tissue-engaging portion 1440. Preferably, at least a portion of the tissue-engaging barbs 1442 extends through a window 1437 while the tissue-engaging portion 1440 is in the insertion configuration to maintain alignment of the tissue-engaging barbs 1442 with the windows 1437 so that upon movement of the tissue-engaging portion 1440 into the tissue-engaging configuration, the tissue-engaging barbs 1442 are positioned to extend radially outwardly through the windows 1437 into an expanded configuration. Once in the expanded configuration, the tissue-engaging barbs 1442 increase tissue engagement of the anchor 1400 with the tissue and/or prevent anchor backout and/or prevent tissue "walking".

Figure 17:
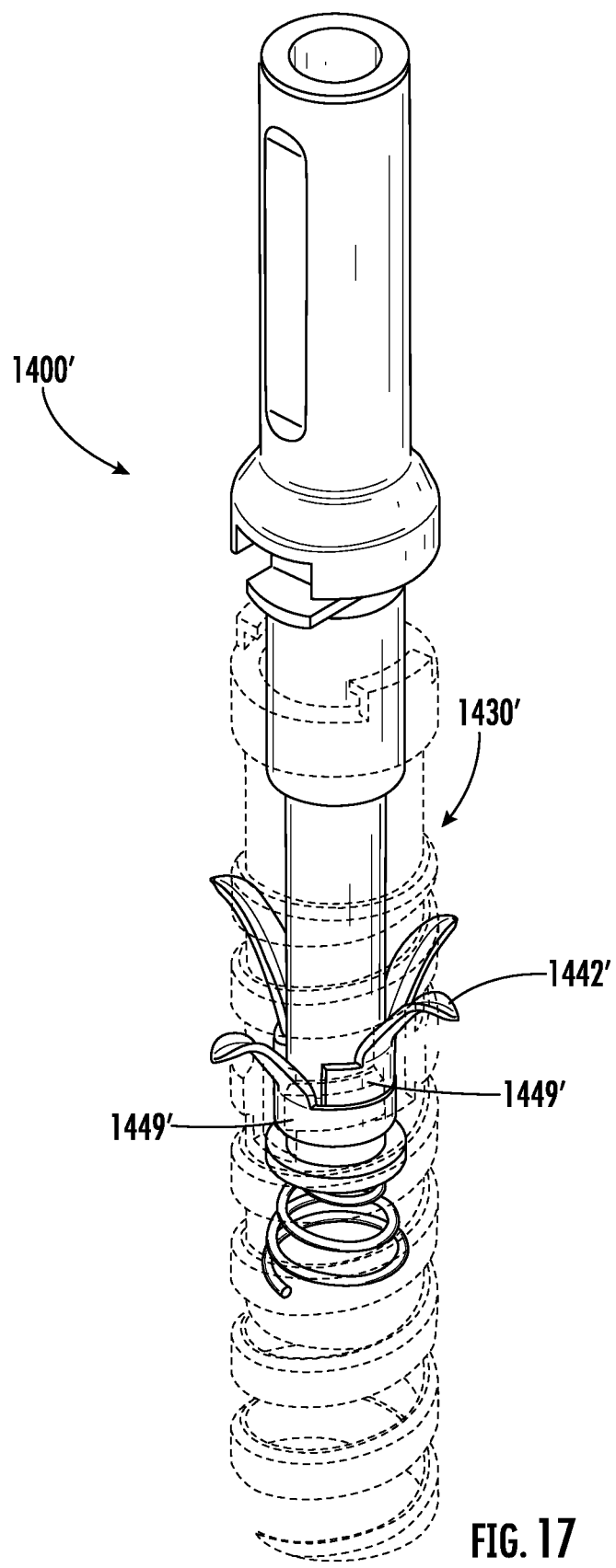
FIG. 17 is a perspective view of another embodiment of an anchor formed in accordance with various principles of the present disclosure, and shown in a tissue-engaging configuration in accordance with various aspects of the present disclosure.
Figure 18:
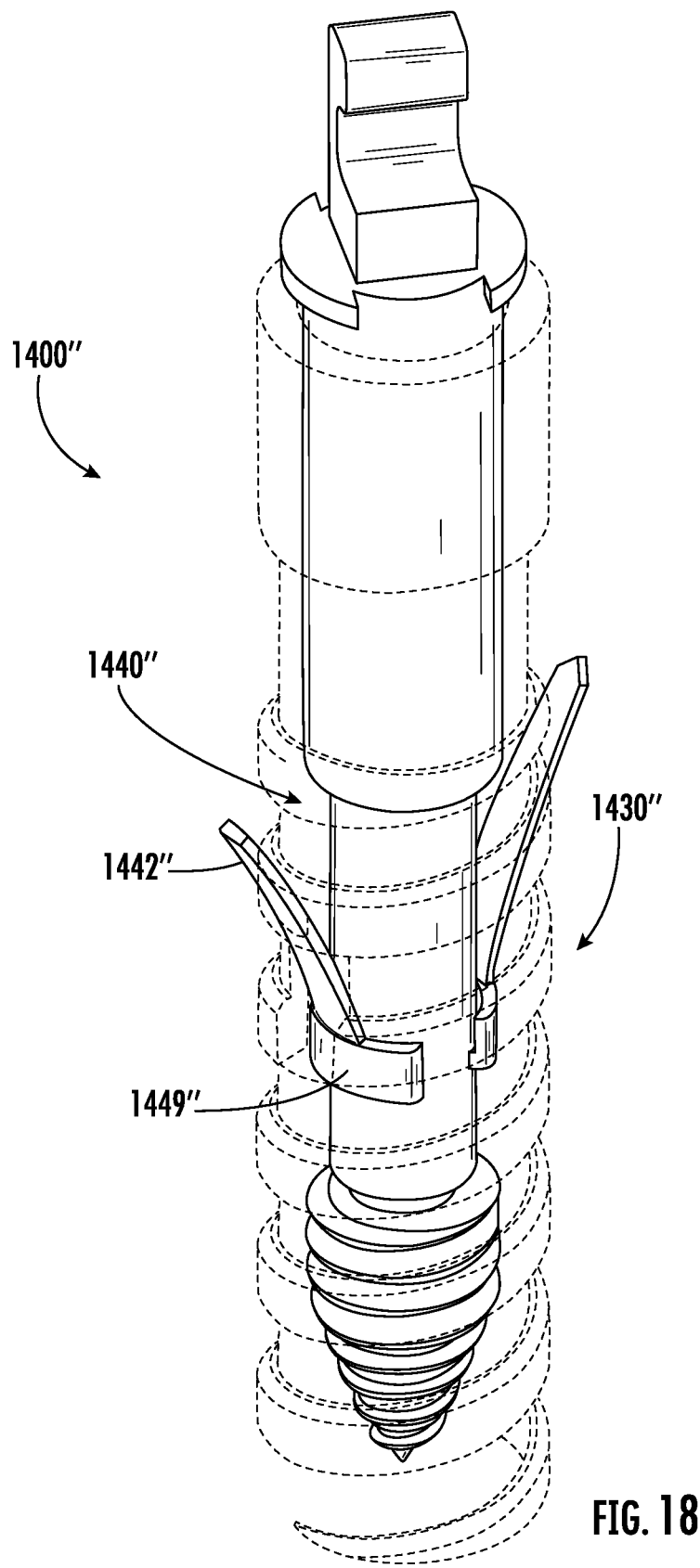
FIG. 18 is a perspective view of another embodiment of an anchor formed in accordance with various principles of the present disclosure, and shown in a tissue-engaging configuration in accordance with various aspects of the present disclosure.

It will be appreciated that various modifications to a tissue-engaging portion 1440 as in the anchor 1400 of FIGS. 14-16 are within the scope of the present disclosure. For instance, as illustrated in FIG. 17, showing an anchor 1400' with an outer drive portion 1430' in phantom, tissue-engaging barbs 1442' may be formed as more than one component. In particular, while each barb 1442 of the embodiment illustrated in FIGS. 14-16 extends from a common ring or collar or base 1449, the barbs 1442' of the embodiment of FIG. 17 may be extend from separate bases 1449' (e.g., more than one semicircular base rather than a circular base). Moreover, the base 1449, 1449', 1449" of the embodiments of FIGS. 14-18 may be in the form of a ring extending to varying extents around the circumference or perimeter of the tissue-engaging portion 1440. As illustrated in the embodiment of FIG. 18, showing an anchor 1400" with an outer drive portion 1430" in phantom, a base 1449" may extend only partially about the circumference or perimeter of the tissue-engaging portion 1440", leaving a visible gap between ends of the open ring of the base 1449". As may be appreciated with reference to the various tissue-engaging barbs 1442, 1442', 1442" illustrated in FIGS. 14-18, the number of barbs provided may vary.

Figure 19:
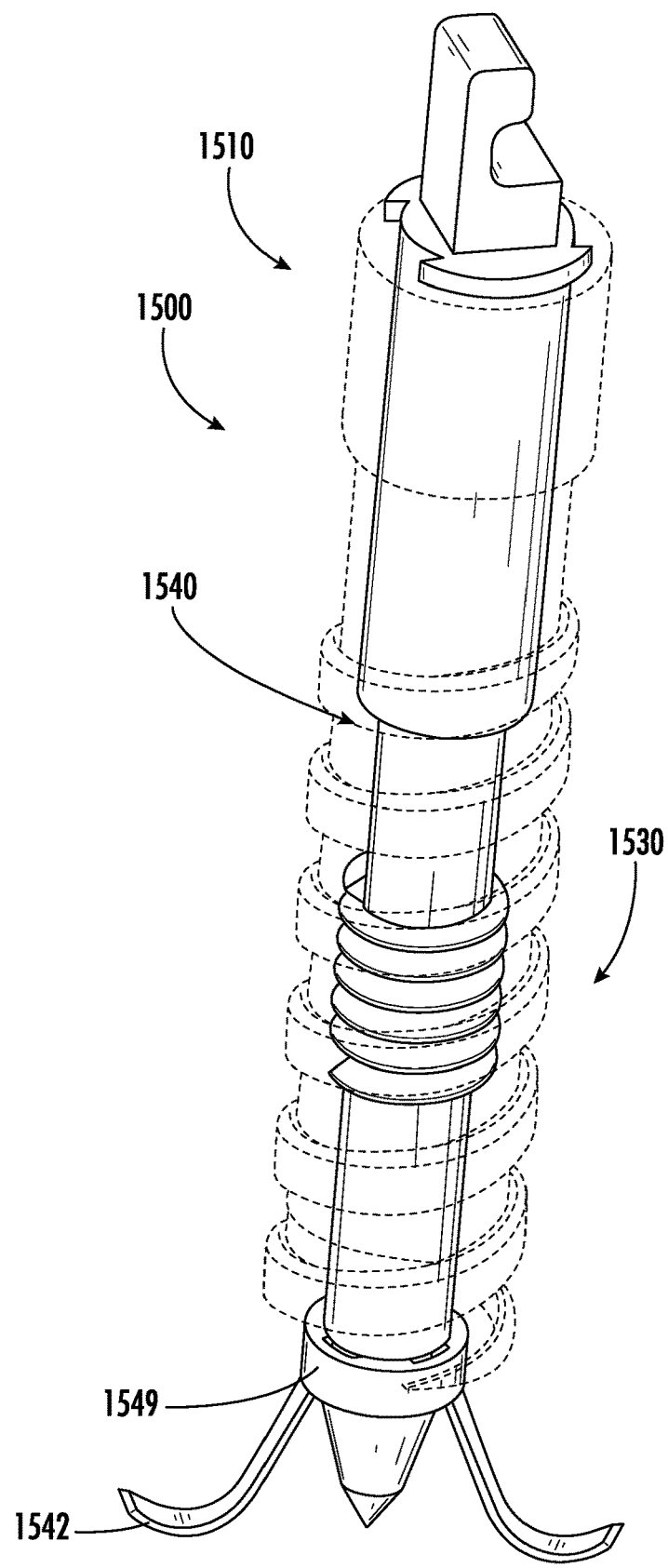
FIG. 19 is a perspective view of another embodiment of an anchor formed in accordance with various principles of the present disclosure, and shown in a tissue-engaging configuration in accordance with various aspects of the present disclosure.
Figure 20:
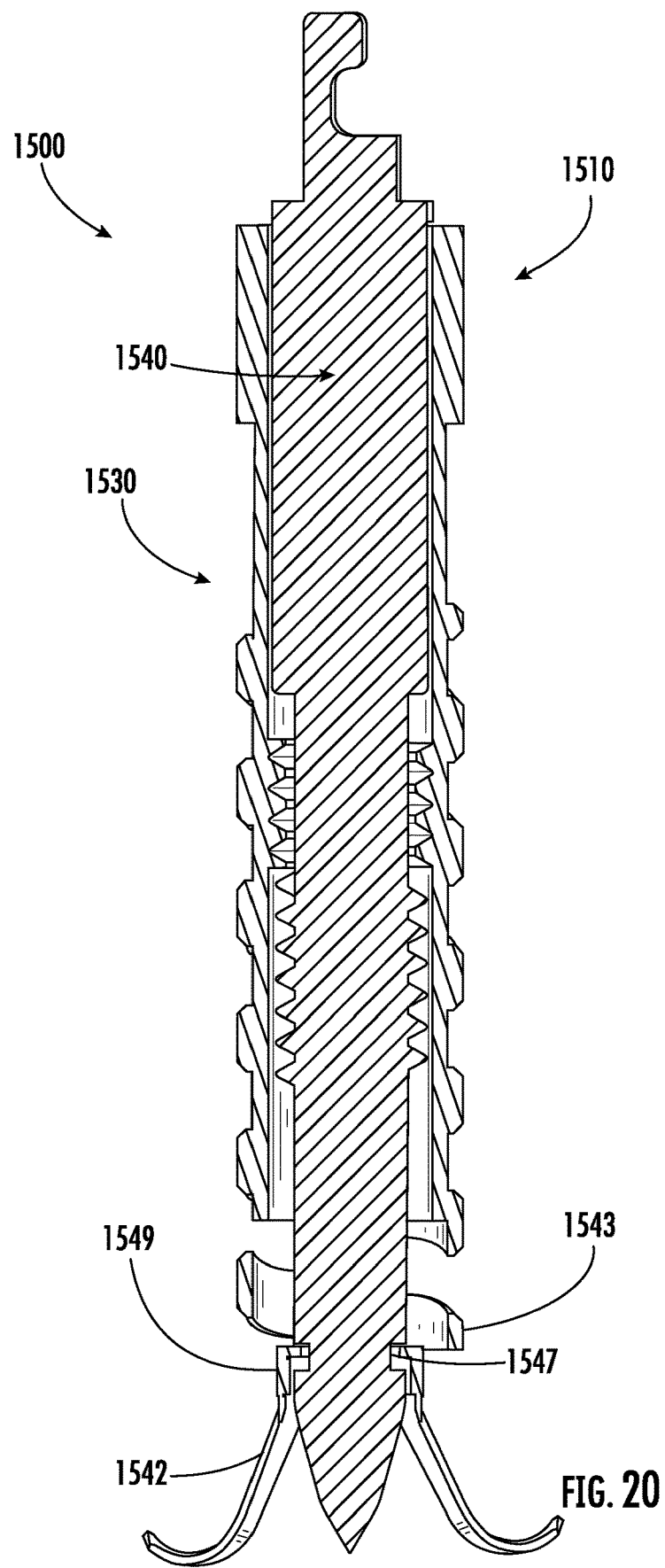
FIG. 20 is a cross-sectional view of an anchor as in FIG. 19.

Instead of barbs extending from an inner tissue-engaging portion 1440 through windows in an outer drive portion 1430, as in the embodiments of FIGS. 14-18, an anchor 1500, as illustrated in FIG. 19 and FIG. 20, includes tissue-engaging barbs 1542 extending from a distal end 1543 of the tissue-engaging portion 1540. During insertion of the anchor 1500, the drive portion 1530 (shown in phantom in FIG. 19) and the tissue-engaging portion 1540 may be rotationally engaged to rotate together. For instance, the anchor head 1510 may be configured to be engaged by the anchor cover 140 such that the anchor cover 140 inhibits relative rotation between the drive portion 1530 and tissue-engaging portion 1540. Once the anchor shaft 1520 has been advanced to a desired position within the tissue, the tissue-engaging portion 1540 may be allowed to rotate relative to the drive portion 1530 (such as by releasing engagement of the anchor cover 140 from the anchor head 1510) to allow relative rotational movement therebetween. As may be appreciated with reference to FIG. 20, the tissue-engaging portion 1540 and drive portion 1530 may be threadedly engaged (such as to hold the tissue-engaging portion 1540 and the drive portion 1530 axially together), and continued rotation of the tissue-engaging portion 1540 relative to the drive portion 1530 allows the tissue-engaging portion 1540 to distally advance with respect to the drive portion 1530 until tissue-engaging barbs 1542 at the distal end 1543 of the tissue-engaging portion 1540 extend outwardly beyond the outer drive portion 1530 to engage within the tissue in which the anchor 1500 has been inserted. It will be appreciated that any of the anchors of FIG. 14-16, 17, or 18 may use a similar threaded engagement of the tissue-engaging portion and drive portion of the anchor 1500, instead of a biasing element, to advance the tissue-engaging barbs into tissue.

It will be appreciated that tissue anchors as described herein may be used in an implantable device as illustrated in FIGS. 1 and 2, as well as with related delivery systems and methods of use, and mechanisms for positioning anchors for annular reconstruction, as well as in conjunction with other implantable devices as described in the following patents and patent applications, each of which is incorporated herein by reference in its entirety for all purposes: U.S. Patent Application Publication No. 2010/0249920, published Sep. 30, 2010, titled "DEVICE FOR TRANSLUMENAL RESHAPING OF A MITRAL VALVE ANNULUS"; U.S. Pat. No. 9,180,005, issued Nov. 10, 2015, titled "ADJUSTABLE ENDOLUMINAL MITRAL VALVE RING"; U.S. Pat. No. 9,192,471, issued Nov. 24, 2015, titled "DEVICE FOR TRANSLUMENAL RESHAPING OF A MITRAL VALVE ANNULUS"; U.S. Pat. No. 9,610,156, issued Apr. 4, 2017, titled "MITRAL VALVE INVERSION PROSTHESES"; U.S. Pat. No. 9,795,480, issued Oct. 24, 2017, titled "RECONFIGURING TISSUE FEATURES OF A HEART ANNULUS"; U.S. Pat. No. 9,848,983, issued Dec. 26, 2017, titled "VALVE REPLACEMENT USING ROTATIONAL ANCHORS"; U.S. Pat. No. 10,321,999, issued Jun. 18, 2019, titled "SYSTEMS AND METHODS FOR RESHAPING A HEART VALVE"; U.S. Pat. No. 10,335,275, issued Jul. 2, 2019, titled "METHODS FOR DELIVERY OF HEART VALVE DEVICES USING INTRAVASCULAR ULTRASOUND IMAGING"; U.S. Pat. No. 10,548,731, issued Feb. 4, 2020, titled "IMPLANTABLE DEVICE AND DELIVERY SYSTEM FOR RESHAPING A HEART VALVE ANNULUS"; and/or U.S. Pat. No. 10,555,813, issued Feb. 11, 2020, titled "IMPLANTABLE DEVICE AND DELIVERY SYSTEM FOR RESHAPING A HEART VALVE ANNULUS".

Various embodiments of tissue anchors configured to secure an implantable device to body tissue have been shown and described. Although embodiments of the present disclosure may be described with specific reference to medical devices and systems (e.g., transluminal devices inserted through a femoral vein or the like) for implanting in heart tissue, it should be appreciated that the disclosed anchors and related systems and methods may also be used in connection with other implantable devices, such as devices implanted in soft tissue and/or tissue with regular movement and which may benefit from enhanced tissue-holding capabilities.

The majority of the anchors disclosed herein can be manufacturing via a CNC (computer numerical control) milling machine and/or a lathe. Some features such as the coils, slits, and interlocking elements can be made using laser cutting and EDM (electrical discharge machining). Most components can be made from polymers (such as polyether ether ketone (PEEK)) or metals (e.g., nitinol, stainless steel, such as 316L stainless steel, etc.). The barb concepts disclosed herein may be made from Nitinol to handle the desired deflection.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A tissue anchor for an implantable device, the tissue anchor having a proximal end and a distal end, the distal end configured for insertion into body tissue, the tissue anchor comprising:
   an anchor head at the proximal end of the anchor; and
   an anchor shaft extending distally from the anchor head to the distal end of the anchor;
   wherein:
   the anchor shaft comprises a tissue-engaging portion and a drive portion, the drive portion configured to drive the anchor shaft into body tissue;
   the tissue-engaging portion and the drive portion of the anchor shaft are engaged at their respective proximal ends in a first configuration inhibiting relative rotation therebetween, and are shiftable into a second configuration in which the respective proximal ends are released from engagement to allow relative rotation therebetween; and the respective proximal ends of the tissue-engaging portion and the drive portion of the anchor shaft are shiftable with respect to each other into the second configuration when the anchor shaft has been inserted into the soft body tissue in an insertion configuration to shift the anchor shaft from the insertion configuration into a tissue-engaging configuration within the soft body tissue, the insertion configuration of the anchor shaft facilitating insertion of the anchor shaft into the soft body tissue, and the tissue-engaging configuration of the anchor shaft enhancing engagement of the anchor shaft with the soft body tissue.

2. The tissue anchor of claim 1, wherein the drive portion has a distal end rotationally coupled with the tissue-engaging portion and positioned within the soft body tissue when the anchor shaft has been fully shifted into the tissue-engaging configuration.

3. The tissue anchor of claim 1, wherein the tissue-engaging portion includes an anchor section which compresses to pinch tissue therebetween when the tissue-engaging portion shifts from the insertion configuration to the tissue-engaging configuration.

4. The tissue anchor of claim 3, wherein the anchor section includes helical coils which move closer together as the tissue-engaging portion shifts from the insertion configuration to the tissue-engaging configuration to grasp tissue between the coils to enhance engagement of the anchor with the tissue.

5. The tissue anchor of claim 1, wherein the tissue-engaging portion includes an anchor section which extends radially outwardly when the tissue-engaging portion shifts from the insertion configuration to the tissue-engaging configuration.

6. The tissue anchor of claim 5, wherein the anchor section buckles outwardly when the tissue-engaging portion shifts from the insertion configuration to the tissue-engaging configuration.

7. The tissue anchor of claim 5, wherein the anchor section flares radially outwardly when the tissue-engaging portion shifts from the insertion configuration to the tissue-engaging configuration.

8. The tissue anchor of claim 7, wherein the anchor section includes barbs which flare outwardly from a stored configuration when the tissue-engaging portion shifts from the insertion configuration to the tissue-engaging configuration.

9. The tissue anchor of claim 7, wherein the anchor section includes a helical coil with ends flaring outwardly when the tissue-engaging portion shifts from the insertion configuration to the tissue-engaging configuration.

10. The tissue anchor of claim 1, wherein the drive portion is positioned within the tissue-engaging portion, and the tissue-engaging portion comprises an outer anchor section movable with respect to the drive portion to shift between the insertion configuration and the tissue-engaging configuration.

11. The tissue anchor of claim 1, wherein the tissue-engaging portion is positioned within the drive portion and includes an anchor section movable with respect to the drive portion from a stored position within the drive portion when the tissue-engaging portion is in the insertion configuration, and an extended position extending outwardly from the drive portion when the tissue-engaging portion is in the tissue-engaging configuration.

12. The tissue anchor of claim 1, wherein a proximal end of the drive portion engages a proximal end of the tissue-engaging portion to inhibit relative rotational movement between the drive portion and the tissue-engaging portion when the tissue-engaging portion is in the insertion configuration, and the proximal end of the drive portion and the proximal end of the tissue-engaging portion are axially movable out of engagement to allow relative rotational movement between the drive portion and the tissue-engaging portion to shift the tissue-engaging portion into the tissue-engaging configuration.

13. The tissue anchor of claim 12, wherein relative rotational movement between the drive portion and the tissue-engaging portion allows axial movement of at least a portion of the tissue-engaging portion relative to the drive portion to allow the tissue-engaging portion to shift into the tissue-engaging configuration.

14. An implantable device comprising:
a frame member; and
at least one anchor coupled to the frame member, the anchor having a proximal end and a distal end, the distal end configured for insertion into soft body tissue;
wherein the anchor comprises:
an anchor head at the proximal end of the anchor;
an anchor shaft extending distally from the anchor head to the distal end of the anchor; and
a tissue-engaging portion having a proximal end shiftable with respect to a proximal end of a drive portion to shift the tissue-engaging portion between an insertion configuration in which the proximal end of the tissue-engaging portion is inhibited from rotating relative to the anchor shaft and facilitating insertion of the anchor shaft into tissue, and a tissue-engaging configuration in which the proximal end of the tissue-engaging portion is released from engagement with the proximal end of the drive portion so that tissue-engaging portion can shift into a configuration along the anchor shaft enhancing engagement of the anchor shaft within the soft body tissue in which the anchor shaft has been inserted.

15. The implantable device of claim 14, further comprising an anchor cover configured to engage the anchor head to facilitate relative movement between the proximal ends of the tissue-engaging portion and the drive portion.

16. The implantable device of claim 15, wherein the anchor cover is configured to hold the tissue-engaging portion axially with respect to the drive portion to allow the drive portion to be moved axially out of engagement with the tissue-engaging portion when the anchor is in the insertion configuration to allow the tissue-engaging portion to move with respect to the drive portion into the tissue-engaging configuration.

17. The implantable device of claim 16, wherein the anchor cover is configured to engage a proximal end of the tissue-engaging portion to inhibit rotation of the proximal end of the tissue-engaging portion relative to a proximal end of the drive portion, while relative rotation between the drive portion and the tissue-engaging portion allows axial movement of a distal end of the tissue-engaging portion to shift the tissue-engaging portion into the tissue-engaging configuration.

18. A method of implanting an implantable device in soft tissue, the method comprising:
advancing an anchor shaft of an anchor coupled to the implantable device into soft tissue; and
after the anchor shaft has been inserted into the soft tissue, causing a first portion of the anchor shaft to shift with respect to a second portion of the anchor shaft from an insertion configuration in which the first portion and the second portion are engaged and inhibited from relative rotation to a tissue-engaging configuration in which the first portion and the second portion are released from engagement to allow a third portion of the anchor shaft to increase purchase on the soft tissue to enhance securement of the implantable device with respect to the soft tissue in which the anchor shaft is positioned.

19. The method of claim 18, wherein the anchor shaft includes a drive portion and a tissue-engaging portion, the method further comprising driving the drive portion into the soft tissue and then causing the tissue-engaging portion to move with respect to the drive portion to increase engagement of the anchor shaft with the soft tissue.

20. The method of claim 19, further comprising rotating the drive portion to cause the tissue-engaging portion to move into the tissue-engaging configuration.

* * * * *